United States Patent
Malberg

(10) Patent No.: US 9,364,338 B2
(45) Date of Patent: Jun. 14, 2016

(54) MODULAR NUCLEUS PULPOSUS PROSTHESIS

(71) Applicant: Marc I. Malberg, Princeton, NJ (US)

(72) Inventor: Marc I. Malberg, Princeton, NJ (US)

(73) Assignee: ResSpond Spinal Systems, Princeton, NJ (US)

( * ) Notice: Subject to any disclaimer, the term of this patent is extended or adjusted under 35 U.S.C. 154(b) by 620 days.

(21) Appl. No.: 13/786,598

(22) Filed: Mar. 6, 2013

(65) Prior Publication Data

US 2013/0184823 A1 Jul. 18, 2013

Related U.S. Application Data

(63) Continuation-in-part of application No. 12/508,356, filed on Jul. 23, 2009, now Pat. No. 8,795,375.

(60) Provisional application No. 61/610,832, filed on Mar. 14, 2012, provisional application No. 61/135,623, filed on Jul. 23, 2008.

(51) Int. Cl.
*A61F 2/44* (2006.01)
*A61F 2/30* (2006.01)
*A61F 2/46* (2006.01)

(52) U.S. Cl.
CPC ............ *A61F 2/442* (2013.01); *A61F 2/4611* (2013.01); *A61F 2002/305* (2013.01); *A61F 2002/30006* (2013.01); *A61F 2002/30224* (2013.01); *A61F 2002/30354* (2013.01); *A61F 2002/30383* (2013.01); *A61F 2002/30461* (2013.01); *A61F 2002/30471* (2013.01); *A61F 2002/30481* (2013.01); *A61F 2002/30507* (2013.01); *A61F 2002/30563* (2013.01); *A61F 2002/30604* (2013.01); *A61F 2002/444* (2013.01); *A61F 2002/448* (2013.01); *A61F 2002/4627* (2013.01); *A61F 2220/0025* (2013.01); *A61F 2220/0033* (2013.01); *A61F 2220/0075* (2013.01); *A61F 2250/0015* (2013.01); *A61F 2250/0018* (2013.01); *A61F 2310/00017* (2013.01);
(Continued)

(58) Field of Classification Search
CPC .................... A61F 2/4465; A61F 2002/444
USPC ........................................ 623/17.11–17.16
See application file for complete search history.

(56) References Cited

U.S. PATENT DOCUMENTS 3,867,728 A 2/1975 Stubstad et al.
3,875,595 A 4/1975 Froning
(Continued)

FOREIGN PATENT DOCUMENTS

DE 197 10 392 C1 7/1999
EP 1925271 A1 5/2008
(Continued)

*Primary Examiner* — Matthew Lawson
(74) *Attorney, Agent, or Firm* — Law Offices of Robert F. Zielinski LLC

(57) ABSTRACT

A modular nucleus pulposus prosthesis having at least two hingedly connected tear drop shaped disc bodies which combined to form a discoid endoprosthetic disc. The complimentary segments are substantially identical including outer circumferential walls roughly equal to a semi-circle aligned along concave-convex inner wall inner walls forming a common "s" shaped border and are positioned to form a generally symmetrical discoid congruent structure which can be placed within the annulus of a spinal disc section. Disc segments may define structures to support, position and secure the segments to one another intradiscally.

40 Claims, 16 Drawing Sheets

(52) U.S. Cl.
CPC .............. *A61F2310/00023* (2013.01); *A61F 2310/00029* (2013.01)

(56) References Cited

U.S. PATENT DOCUMENTS

| | | |
|---|---|---|
| 4,349,921 A | 9/1982 | Kuntz |
| 4,772,287 A | 9/1988 | Ray et al. |
| 4,904,260 A | 2/1990 | Ray et al. |
| 4,911,718 A | 3/1990 | Lee et al. |
| 4,917,704 A | 4/1990 | Frey et al. |
| 4,932,969 A | 6/1990 | Frey et al. |
| 4,955,908 A | 9/1990 | Frey et al. |
| 5,041,114 A | 8/1991 | Chapman et al. |
| 5,047,055 A | 9/1991 | Boa et al. |
| 5,071,437 A | 12/1991 | Steffee |
| 5,123,926 A | 6/1992 | Pisharodi |
| 5,171,280 A | 12/1992 | Baumgartner |
| 5,171,281 A | 12/1992 | Parsons et al. |
| 5,192,326 A | 3/1993 | Bao et al. |
| 5,314,477 A | 5/1994 | Marnay |
| 5,401,269 A | 3/1995 | Bittner-Janz et al. |
| 5,443,514 A | 8/1995 | Steffee |
| 5,458,642 A | 10/1995 | Beer et al. |
| 5,458,643 A | 10/1995 | Oka et al. |
| 5,505,732 A | 4/1996 | Michelson |
| 5,507,816 A | 4/1996 | Bullivant |
| 5,522,899 A | 6/1996 | Michelson |
| 5,534,028 A | 7/1996 | Bao et al. |
| 5,545,229 A | 8/1996 | Parsons et al. |
| 5,549,679 A | 8/1996 | Kuslich |
| 5,556,431 A | 9/1996 | Buttner-Janz |
| 5,562,736 A | 10/1996 | Ray et al. |
| 5,571,189 A | 11/1996 | Kuslich |
| 5,593,409 A | 1/1997 | Michelson |
| 5,609,635 A | 3/1997 | Michelson |
| 5,645,597 A | 7/1997 | Krapiva |
| 5,674,294 A | 10/1997 | Bainville et al. |
| 5,674,295 A | 10/1997 | Ray et al. |
| 5,676,701 A | 10/1997 | Yuan et al. |
| 5,702,450 A | 12/1997 | Bisserie |
| 5,702,454 A | 12/1997 | Baumgartner |
| 5,716,415 A | 2/1998 | Steffee |
| 5,755,797 A | 5/1998 | Baumgartner |
| 5,772,661 A | 6/1998 | Michelson |
| 5,776,199 A | 7/1998 | Michelson |
| 5,824,093 A | 10/1998 | Ray et al. |
| 5,860,973 A | 1/1999 | Michelson |
| 5,865,846 A | 2/1999 | Bryan et al. |
| 5,893,889 A | 4/1999 | Harrington |
| 5,919,236 A | 7/1999 | Pfaff et al. |
| 5,984,967 A | 11/1999 | Zdeblick et al. |
| 6,001,130 A | 12/1999 | Bryan et al. |
| 6,039,763 A | 3/2000 | Shelokov |
| 6,096,038 A | 8/2000 | Michelson |
| 6,110,210 A | 8/2000 | Norton et al. |
| 6,146,422 A | 11/2000 | Lawson |
| 6,156,037 A | 12/2000 | LeHuec et al. |
| 6,156,067 A | 12/2000 | Bryan et al. |
| 6,159,211 A | 12/2000 | Boriani et al. |
| 6,187,048 B1 | 2/2001 | Milner et al. |
| 6,193,757 B1 | 2/2001 | Foley et al. |
| D439,162 S | 3/2001 | Juhng |
| 6,251,140 B1 | 6/2001 | Marino et al. |
| 6,258,125 B1 | 7/2001 | Paul et al. |
| 6,264,695 B1 | 7/2001 | Stoy |
| 6,302,914 B1 | 10/2001 | Michelson |
| 6,371,990 B1 | 4/2002 | Ferree |
| 6,387,130 B1 | 5/2002 | Stone et al. |
| 6,419,704 B1 | 7/2002 | Ferree |
| 6,423,083 B2 | 7/2002 | Reiley et al. |
| 6,443,988 B2 | 9/2002 | Felt et al. |
| 6,447,544 B1 | 9/2002 | Michelson |
| 6,468,311 B2 | 10/2002 | Boyd et al. |
| 6,482,234 B1 | 11/2002 | Weber et al. |
| 6,488,710 B2 | 12/2002 | Besselink |
| 6,533,818 B1 | 3/2003 | Weber et al. |
| 6,595,998 B2 | 7/2003 | Johnson et al. |
| 6,620,196 B1 | 9/2003 | Trieu |
| 6,652,587 B2 | 11/2003 | Felt et al. |
| 6,726,720 B2 | 4/2004 | Ross et al. |
| 6,726,721 B2 | 4/2004 | Stoy et al. |
| 6,733,535 B2 | 5/2004 | Michelson |
| 6,740,093 B2 | 5/2004 | Hochschuler et al. |
| 6,764,514 B1 | 7/2004 | Li et al. |
| 6,855,167 B2 | 2/2005 | Shimp et al. |
| 6,896,701 B2 | 5/2005 | Boyd et al. |
| 6,964,686 B2 | 11/2005 | Gordon |
| 7,001,431 B2 | 2/2006 | Bao et al. |
| 7,008,452 B2 | 3/2006 | Hawkins |
| 7,018,413 B2 | 3/2006 | Kruger |
| 7,267,690 B2 | 9/2007 | Felt |
| 7,270,679 B2 | 9/2007 | Istephanous et al. |
| 7,309,357 B2 | 12/2007 | Kim |
| 7,326,250 B2 | 2/2008 | Beaurain et al. |
| 7,503,933 B2 | 3/2009 | Michelson |
| 7,563,284 B2 | 7/2009 | Coppes et al. |
| 7,591,853 B2 | 9/2009 | Felt et al. |
| 7,695,515 B2 | 4/2010 | Sweeney |
| 7,731,753 B2 | 6/2010 | Reo et al. |
| 7,771,478 B2 | 8/2010 | Navarro et al. |
| 7,794,499 B2 | 9/2010 | Navarro et al. |
| 2002/0026244 A1 | 2/2002 | Trieu |
| 2002/0128715 A1 | 9/2002 | Bryan et al. |
| 2002/0183848 A1 | 12/2002 | Ray et al. |
| 2003/0055506 A1 | 3/2003 | Stoy et al. |
| 2003/0135279 A1 | 7/2003 | Michelson |
| 2003/0204260 A1 | 10/2003 | Ferree |
| 2003/0233146 A1 | 12/2003 | Grinberg et al. |
| 2004/0010318 A1 | 1/2004 | Ferree |
| 2004/0019354 A1 | 1/2004 | Johnson et al. |
| 2004/0054411 A1 | 3/2004 | Kelly et al. |
| 2004/0054413 A1 | 3/2004 | Higham et al. |
| 2004/0064144 A1 | 4/2004 | Johnson et al. |
| 2004/0098131 A1 | 5/2004 | Bryan et al. |
| 2004/0111155 A1 | 6/2004 | Ferree |
| 2004/0186576 A1 | 9/2004 | Biscup et al. |
| 2004/0220580 A1 | 11/2004 | Johnson et al. |
| 2004/0220672 A1 | 11/2004 | Shadduck |
| 2004/0230198 A1 | 11/2004 | Manzi et al. |
| 2004/0243241 A1 | 12/2004 | Istephanous et al. |
| 2004/0254643 A1 | 12/2004 | Jackson |
| 2005/0010290 A1 | 1/2005 | Hawkins |
| 2005/0015150 A1 | 1/2005 | Lee |
| 2005/0033437 A1 | 2/2005 | Bao et al. |
| 2005/0055097 A1 | 3/2005 | Grunberg et al. |
| 2005/0107880 A1 | 5/2005 | Shimp et al. |
| 2005/0154463 A1 | 7/2005 | Trieu |
| 2005/0154465 A1 | 7/2005 | Hodges et al. |
| 2005/0203599 A1 | 9/2005 | Garabedian et al. |
| 2005/0228400 A1 | 10/2005 | Chao et al. |
| 2005/0273178 A1 | 12/2005 | Boyan et al. |
| 2006/0106462 A1 | 5/2006 | Tsou |
| 2006/0111783 A1* | 5/2006 | Aflatoon ............... A61F 2/4425 623/17.14 |
| 2006/0142858 A1 | 6/2006 | Colleran et al. |
| 2006/0149381 A1 | 7/2006 | Kim |
| 2006/0167550 A1 | 7/2006 | Snell et al. |
| 2006/0189999 A1 | 8/2006 | Zwirkoski |
| 2006/0195191 A1 | 8/2006 | Sweeney, II et al. |
| 2006/0247778 A1 | 11/2006 | Ferree et al. |
| 2006/0247781 A1 | 11/2006 | Francis |
| 2006/0259144 A1 | 11/2006 | Trieu |
| 2006/0264965 A1 | 11/2006 | Shadduck et al. |
| 2006/0293756 A1 | 12/2006 | Felt |
| 2007/0027546 A1 | 2/2007 | Palm et al. |
| 2007/0032874 A1 | 2/2007 | Lee et al. |
| 2007/0073400 A1 | 3/2007 | Paul |
| 2007/0088362 A1 | 4/2007 | Bonutti et al. |
| 2007/0162130 A1 | 7/2007 | Rashbaum et al. |
| 2007/0244485 A1 | 10/2007 | Greenhalgh et al. |
| 2007/0265652 A1 | 11/2007 | Assell et al. |
| 2008/0039942 A1 | 2/2008 | Bergeron |
| 2008/0046082 A1 | 2/2008 | Lee |
| 2008/0051902 A1 | 2/2008 | Dwyer |

(56) References Cited

U.S. PATENT DOCUMENTS

| | | |
|---|---|---|
| 2008/0058944 A1 | 3/2008 | Duplessis et al. |
| 2008/0065220 A1 | 3/2008 | Alleyne et al. |
| 2008/0077153 A1 | 3/2008 | Pernsteiner et al. |
| 2008/0086142 A1 | 4/2008 | Kohm et al. |
| 2008/0114371 A1 | 5/2008 | Kluger |
| 2008/0119853 A1 | 5/2008 | Felt et al. |
| 2008/0133017 A1 | 6/2008 | Beyar et al. |
| 2008/0140086 A1 | 6/2008 | Moore et al. |
| 2008/0140206 A1 | 6/2008 | Felt |
| 2008/0208196 A1 | 8/2008 | Daum |
| 2008/0208343 A1 | 8/2008 | Felt |
| 2008/0312743 A1* | 12/2008 | Vila .................. A61F 2/442 623/17.16 |
| 2009/0125033 A1 | 5/2009 | Hushka et al. |
| 2009/0248159 A1 | 10/2009 | Aflatoon |
| 2010/0324689 A1 | 12/2010 | Obrigkeit et al. |
| 2011/0082555 A1 | 4/2011 | Martz et al. |

FOREIGN PATENT DOCUMENTS

| | | |
|---|---|---|
| WO | 2005067824 A1 | 7/2005 |
| WO | 2006116851 A1 | 11/2006 |
| WO | 2006127846 A2 | 11/2006 |

* cited by examiner

MODULAR NUCLEUS PULPOSUS PROSTHESIS

CROSS-REFERENCE TO RELATED APPLICATIONS

The present patent application is based on Provisional Application Ser. No. 61/610,832, filed Mar. 14, 2012 and is a continuation-in-part of U.S. patent application Ser. No. 12/508,356, filed on Jul. 23, 2009, which claims the benefit of priority of Provisional Application Ser. No. 61/135,623, filed Jul. 23, 2008, the entireties of which are hereby incorporated by reference.

FIELD OF THE DISCLOSURE

This disclosure relates generally to human prostheses, and more specifically to spinal column vertebral disc prostheses otherwise known as or referred to as spinal disc endoprostheses. The disclosure also relates to surgical tools and procedures for preparing the patient to receive a spinal disc endoprosthesis and for implanting the endoprosthesis in the patient's spine.

BACKGROUND OF THE DISCLOSURE AND PRIOR ART

Intervertebral or spinal discs, lie between adjacent vertebrae which are the interlocking bones of the spine that are stacked on top of one another. Each disc forms a fibrocartilaginous joint to enable slight movement of the vertebrae, and acts as a ligament to hold the vertebrae together. Individual discs enable very limited vertebral motion such as extension and flexion; however, considerable motion is possible when several discs move in tandem. In addition to providing the shock absorbing function, these discs enable the entire vertebrae or portions thereof to flex, bend, and twist.

In humans, there is one disc between each pair of vertebrae, except for the first cervical segment, the atlas. The atlas is a ring around the roughly cone-shaped extension of the axis or second cervical segment. The axis acts as a post around which the atlas can rotate, enabling the neck to swivel. There are a total of twenty-three discs in the human spine, which are most commonly identified by specifying the particular vertebrae they separate. For example, the disc between the fifth and sixth cervical vertebrae is designated "C5-C6", the disc between the fourth and fifth lumbar vertebrae would be "L4-L5" and so on.

An intervertebral disc consists of two parts, the annulus fibrosis and the nucleus pulposus. The annulus fibrosus surrounds and, therefore "contains" the inner nucleus pulposus. The annulus fibrosus consists of several layers of fibrocartilage. The strong annular fibers of the capsule contain the nucleus pulposus and distribute pressure evenly across the disc. The nucleus pulposus contains loose fibers suspended in a mucoprotein gel having the consistency of saturated sponge. The nucleus has a high water content (about 80-85%), with the remainder made up mostly of proteoglycan, type II collagen fibers and elastin fibers. The proteoglycan functions to trap and hold the water, which is what gives the nucleus its strength and resiliency. The nucleus pulposus exerts constant "outward" pressure on the surrounding annulus fibrosus, even in the supine position, thus maintaining appropriate disc height.

The nucleus pulposus acts as a shock absorber, absorbing the impact of the body's daily activities and keeping the adjacent vertebrae separated, thus serving to protect the vertebrae, brain, and other structures such as the nerves extending from the spinal column. The intervertebral disc has multiple functions. It preserves spinal stability, allows for flexibility and absorbs the shock of repeated loading transmitted to the vertebral endplates during daily activity. It is, in part, analogous to a hydraulic device. The annulus fibrosis is the gasket, the nucleus pulposus is the pressurized hydraulic fluid and the pistons are the adjacent endplates that can be separated or approximated through a limited range to accommodate load and motion. Injury or weakness of the annulus fibrosis results in bulging of the annulus fibrosis from the pressure of the nucleus pulposus. If the bulge extends into the spinal canal the result is compression of the nerve root or the spinal elements resulting in neurologic pain and muscle weakness. A complete tear of the annulus fibrosis allows part of the nucleus pulposus to "escape" which can acutely result in even more severe pain and neurologic deficit. It also results in loss of disc height and bulging of the entire annulus fibrosis, like a deflated tire, which initiates the "degenerative cascade" to chronic, disabling back pain and spinal stenosis, a condition of circumferential pressure on the spinal cord. This condition results in both back pain and neurologic damages that restrict the ability to stand and walk and can even lead to loss of bowel and bladder control. Reconstructive surgery is frequently indicated.

Spinal discs can fail or rupture through aging, injury, and illness. For instance, as people age, the nucleus pulposus begins to dehydrate, which limits its ability to absorb shock. The annulus fibrosus gets weaker with age and begins to tear. While this may not cause pain in some people, in others one or both of these may cause chronic pain.

Spinal discs are structures that are, by and large, prone to degenerative changes associated with wear and tear aging, misuse (e.g. smoking) and repeated trauma, such as frequent heavy lifting as well as genetic predisposition. These degenerative changes can cause the loss of normal structure and/or function. Over time the collagen or protein structure of the annulus fibrosus weakens and may become structurally unsound. Additionally, both water and proteoglycans (i.e. molecules that attract water content) decreases. Age-related changes that cause degenerative disc disease include a loss of fluid in the discs and tiny tears or cracks in the annulus or capsule of the disc. A sudden or acute injury leading to a herniated disc may also begin the degeneration process. Stress from motion may also result in a disc problem (e.g. herniation). These changes are linked and lead to the disc's inability to handle mechanical stress and the breakdown of the discs can result in back or neck pain, weakness, and loss of function as well as osteoarthritis, herniated disc, or spinal stenosis.

One generally refers to the gradual dehydration of the nucleus pulposus as degenerative disc disease. Degenerative disc disease is somewhat of a misnomer in that it is not really a disease, but rather a degenerative cascade that at times can produce pain from a damaged disc. Degenerative disc disease can take place throughout the spine, but it most often occurs in the discs in the lumbar region and the cervical region. Herniation of a spinal disc and the often resultant symptoms of intractable pain, weakness, sensory loss, incontinence and progressive arthritis are among the most common of debilitating afflictions associated with this process. As used herein, degenerative disc disease will be understood to refer to all chronic or acute states of physical and physiological changes of the spinal discs resulting in pain or dysfunction.

When the annulus fibrosus weakens due to an injury or the aging process, the nucleus pulposus can begin to bulge the annulus fibrosis or even extrude through the tear. This is called disc herniation. Near the posterior side of each disc, all along the spine, major spinal nerves extend out to different organs, tissues, extremities etc. It is very common for the herniated disc to press against these nerves, commonly known as a pinched nerve, causing radiating pain, numbness, tingling, and diminished strength and/or range of motion.

In addition, the contact of the inner nuclear material, which contains inflammatory proteins, with a nerve can also cause significant pain referred to as radicular pain or radiculitis. A common form of radiculitis is sciatica, a radicular pain that radiates along the sciatic nerve from the lower spine to the lower back, gluteal muscles, back of the upper thigh, calf, and foot as often secondary to nerve root irritation from a spinal disc herniation or from osteophytes in the lumbar region of the spine. Pain due to the inability of the dehydrating nucleus pulposus to absorb shock is called axial pain or disc space pain.

Herniated discs go by many names and these can mean different things to different medical professionals. A slipped disc, ruptured disc, or a bulging disc can all refer to the same medical condition.

Typically, patients suffering from degenerative disc disease, including disc herniation, may be treated conservatively through a regimen of pain medications, physical therapy, exercise, immobilization, acupuncture and combinations of the foregoing. In the case of a herniated disc, if a patient's condition does not improve after conservative treatment, and if there is clear physical evidence of nerve root or spinal cord compression apparent and confirmed through radiological means, surgical removal of the herniated disc may be indicated. The process of discectomy—as the name implies—involves the simple removal of the disc without attempt to replace or repair the malfunctioning unit.

Statistics suggest that surgical techniques such as discectomies, are likely to result in short-term relief, but will not prevent the progressive deterioration of the patient's condition in the long run. Through better pre-operative procedures and diagnostic studies, long-term patient results have improved somewhat. But it has become clear that unless the removed disc is replaced or the spine is otherwise properly supported, the degenerative cascade accelerates and further degeneration of the patient's condition will almost certainly occur.

In the mid-1950's and 60's, Cloward and Smith & Robinson popularized anterior surgical approaches to the cervical spine for the treatment of cervical degenerative disc disease and related disorders of the vertebrae, spinal cord and nerve root; these surgeries involved disc removal followed by interbody fusion with a bone graft. It was noted by Robinson (Robinson, R. A.: The Results of Anterior Interbody Fusion of the Cervical Spine, J. Bone Joint Surg., 440A: 1569-1586, 1962) that after surgical fusion, osteophyte (bone spur) reabsorption at the fused segment might take place. However, it has become increasingly apparent that unfused vertebral segments at the levels above and below the fused segment degenerate at accelerated rates as a direct result of this fusion. This has led some surgeons to perform discectomy alone, without fusion, by a posterior approach in the neck of some patients. However, as has occurred in surgeries involving the lower back where discectomy without fusion is more common as the initial treatment for disc herniation syndromes, progressive degeneration at the level of disc excision is the rule rather than the exception. Premature degenerative disc disease at the level above and below the excised disc can and does occur.

Discectomy procedures have inherent risks since the portion of the disc to be removed is immediately adjacent the nerve root and any damage to the nerve root is clearly undesirable. Further, the long-term success of discectomy procedures is not always certain due to the loss of nucleus pulposus which can lead to a loss in disc height. Loss of disc height increases loading on the facet joints which can result in deterioration of the joint and lead to osteoarthritis and ultimately to foraminal stenosis, pinching the nerve root. Loss of disc height also increases the load on the annulus as well. As the annulus fibrosis has been shown to have limited healing capacity subsequent to discectomy. A compromised annulus may lead to accelerated disc degeneration which may require spinal interbody fusion or total disc replacement.

Spine surgery occasionally involves fusion of the spine segments. In addition to the problems created by disc herniation, traumatic, malignant, infectious and degenerative syndromes of the spine can be treated by fusion. Other procedures can include bone grafts and heavy duty metallic rods, hooks, plates and screws being appended to the patient's anatomy; often they are rigidly and internally fixed. None provide for a patient's return to normal functioning. Though these procedures may solve a short-term problem, they can cause other, longer term, problems.

A number of attempts have been made to solve some of the problems described above by providing a patient with spinal disc prostheses, or artificial discs of one sort or another in an effort to prevent the longer term problems.

For example, Steffee, U.S. Pat. No. 5,031,437, describes a spinal disc prosthesis having upper and lower rigid flat plates and a flat elastomeric core sandwiched between the plates. Frey et al., U.S. Pat. Nos. 4,917,704 and 4,955,908, disclose intervertebral prostheses, but the prostheses are described as solid bodies.

U.S. Pat. Nos. 4,911,718 and 5,171,281 disclose resilient disc spacers, but no inter-connective or containing planes or like elements are suggested, and sealing the entire unit is not taught.

U.S. Pat. No. 6,156,067 discloses an endoprosthesis having a resilient body formed of one or more materials which may vary in stiffness from a relatively stiff exterior annular gasket portion to a relatively supple central nucleus portion.

U.S. Pat. No. 6,964,686 discloses implantable intervertebral disc replacement prosthesis having a deformable flexure with disc member and lower and upper disc supports communicating with one another to provide support to the disc.

A more recent alternative to spinal fusion is replacement of the damaged disc with a motion preservation device, which includes either a nucleus or total disc replacement. The rationale for the development of the artificial disc is to prevent adjacent segment disease. Artificial disc devices can be broadly divided into two categories, those that replace the nucleus only, leaving the annulus and vertebral body end plates intact and those that involve replacement of the disc and addition of prosthetic end plates. Both strategies are directed at restoration of intervertebral disc function. Prosthetic nuclei are described, for example, in U.S. Pat. Nos. 5,047,055 and 5,192,326. United States Patent application US2002/0183848 also discloses a prosthetic spinal disc nucleus that has a hydrogel core surrounded by a constraining jacket.

There are also several different types of commercially available prosthetic devices for use in the cervical or lumbar segments of the spine designed for total disc replacement. For example, the Prodisc® and the Charite® disc are composites of cobalt chromium end plates with a polyethylene core. The Prodisc® is described in U.S. Pat. No. 5,314,477 and the Charite® disc is described in U.S. Pat. Nos. 5,401,269 and 5,556,431. The Prestige® disc is another type of artificial disc that comprises a metal on metal design with a ball and trough articulation. Another type of artificial disc that is gaining popularity in the cervical spine is the Bryan® disc, described in several United States Patent applications including 2004/0098131; 2004/00544411; and 2002/0128715. The Bryan® disc is a composite artificial disc with a low friction, wear resistant, elastic nucleus that articulates with two circular metal plates.

It will be appreciated that prior art attempts at intervertebral endoprosthesis have inherent limitations and have been met with limited success. It will likewise be appreciated that there is a need to overcome the limitations of the prior art and to provide an intervertebral endoprosthesis that avoid the problems inherent in the known prior art.

It is an advantage of the present disclosure to provide a vertebral disc endoprosthesis which will perform effectively and efficiently within a patient's spine over a long period of time, and which will not encourage degeneration of or cause damage to adjacent natural disc parts.

It is another advantage to provide a vertebral disc endoprosthesis which does not require external pins or other common external mechanical hinge elements, yet which permits natural motion of the prosthetic parts and the adjacent natural anatomy.

It is a related objective to provide a new vertebral disc endoprosthesis surgical procedure which will decrease post-operative recovery time and inhibit post-operative disc, vertebral body and spinal joint degeneration.

Another advantage of the present disclosure is to provide an intervertebral disc prosthesis that assists in alleviating the symptoms of degenerative disc disease without sacrificing normal spinal biomechanics.

Yet another advantage of the present disclosure is a prosthesis that is easily implanted and mimics both the motion and the stiffness of a normal disc.

It is yet another advantage to provide a method of installing the endoprosthesis so as to accurately mate the endoprosthesis with a preexisting formed bone surface.

An associated advantage is to provide an endoprosthesis which will not encourage bone attachment to, and growth upon, adjacent outer surfaces of the endoprosthesis.

Yet another advantage is to provide a vertebral endoprosthesis in which the parts are non-oncogenic.

Still another advantage is to provide a vertebral disc endoprosthesis having a modulus of elasticity compatible with bone to accommodate shocks and other forces applied to the spine.

Another advantage is to provide a highly effective vertebral endoprosthesis which defines several disc endoprostheses.

A related advantage is to provide these elements in a pre-assembled array for implantation in a patient.

A related advantage is to provide these elements in a pre-assembled array that may be hinged to facilitate in-site assembly.

Still another advantage is to provide two elements with a closure mechanism that securely fastens the elements to each other.

Another advantage of the present disclosure is to provide tools and methods for inserting and positioning spinal disc members into a patient and may also include tools and methods for securing the spinal disc members together.

SUMMARY OF THE DISCLOSURE

The present disclosure relates to a spinal disc endoprosthesis and to associated tools and methods for replacing the intervertebral disc. The endoprosthesis is generally discoid in appearance with rounded edge walls and has a segmented body formed of complimentary "yin-yang" shaped complimentary mirror imaged sections that are mateably arranged along a common border in a congruent manner along the latitudinal axis and which limits lateral and twisting movement of the sections. In the present disclosure, the complimentary imaged sections are operatively joined to one another at their respective head and tail ends via a hinge and/or other flexible connection which facilitates articulation about an axis. As used herein, hinge may be construed to include other articulation mechanism including but not limited to ball-and-socket assemblies, springs, swivels, flexible joints, universal joints, pivot assemblies and their mechanical equivalents. The endoprosthesis may be fabricated of one or more materials which may vary in stiffness but are preferably of uniform stiffness and density. Preferred endoprosthetic materials include biocompatible metals such as orthopedic metal alloys, biocompatible ceramics, biocompatible silicone elastomers and combinations of the foregoing. The endoprosthesis may be manufactured from other biocompatible materials that are suitably rigid to withstand the pressures exerted upon the endoprosthesis by the vertebrae. Other examples of materials that may be used to manufacture the endoprosthesis include, but are not limited to, PEEK (polyether ether ketone), titanium and allograft bone. It may be appreciated that PEEK has not traditionally been considered a shape memory polymer; however, recent advances in processing have allowed shape memory behavior in PEEK with mechanical activation. This technology has expanded to applications in orthopedic surgery and may be suitable in the present invention.

In one aspect, the present disclosure can comprise at least two generally complimentary spinal disc segments combined to form an endoprosthetic disc. In an embodiment, the complimentary segments are similar with each having one-half of the familiar "yin-yang" shape including on one side, an outer circumferential wall with generally uniform "radius of curvature" roughly equal to a semi-circle and with each segment further having an inner wall (relative to the combined segments assembly) with a concave wall portion adjacent a convex wall portion and which is generally positioned along the diameter of the semi-circular arcs of the outer walls.

The spinal disc segments of the present disclosure are combined along their inner walls to share a common border and to form a generally congruent structure which is positioned within the annular ring structure or annulus of a spinal disc section which is to be replaced or repaired. As used herein, congruent means the completed generally symmetrical discoid structure of the spinal endoprosthesis of the present disclosure formed of two or more disc segment members. Upon removal of the existing damaged nucleus pulposus and/or by occupying the space thereof, the complimentary spinal disc segments are inserted, positioned and secured preferably using tools specific to the individual segments. In this regard, and for ease of reference, the segments are surgically inserted one at a time with the initial segment being referred to herein as the first disc member and the following segment being referred to as the second disc member.

In other embodiments, each spinal disc segment may optionally further define a groove, notch, boss, conduit, channel, chamber and combinations thereof to support, position and secure the segments to one another after the segments are disposed intradiscally (i.e. within the annulus of the vertebral body in place of the nucleus pulposus) as well as to assist in the posterior surgical insertion and placement of the segments within a patient's vertebral column. In yet other preferred embodiments, the discoid segments are hingedly connected along respective trailing and leading edges so as to facilitate introduction into the spinal space and assembly into via a wire "come-along" mechanism operatively connected to an insertion tool. In these embodiments, the discoid segments will be introduced into the spinal space in an open "un-folded" configuration. As the wire come-along mechanism is operated via the insertion tool, the two segments are drawn towards one another to form the discoid shape with the hinge serving as a pivot point and stabilizer. Additionally the complimentary abutting faces may define bead and recess type connectors for "snapping" the two discoid segments together. The optional supporting, positioning and securing structures are exemplary and are not exhaustive. Other supporting, positioning and securing structures and devices including but not limited to elastomeric compounds, bio-compatible glues, bio-compatible fasteners, and magnets may also be employed to achieve the invention disclosed herein and are within the scope the appended claims.

In another aspect, the present disclosure can further comprise surgical tools to enable the intradiscal placement of the first and second disc members and to methods of use of said tools. In an embodiment, the tools define structures for detachably mounting the disc members and for placing the first and second members in alignment with each other which may also define features for securing the first and second disc members together.

In yet another aspect, the present disclosure can comprise a system and method for replacing the nucleus pulposus with first and second disc members using the surgical tools adapted for the intradiscal placement of the first and second disc members, for placing hingedly connected first and second members in alignment with each other which may also define methods of assembling the first and second disc members to form a discoid within the intradiscal space.

In use, a damaged disc is surgically removed and the replacement endoprosthesis is inserted between adjacent vertebral bodies in a patient's spine employing a surgical approach similar to a posterior lumbar interbody fusion.

Posterior lumbar interbody fusion (PLIF) is a surgical technique that involves removing a disc and fusing vertebrae together in the lower back (the lumbar region). The procedure involves a surgeon making an incision in the midline of the back. After cutting into the middle of the layer of muscle and ligament that sits on either side of the spine, the attachments to the spinous process and lamina are freed. Using a special instrument that removes small fragments of bone, the lamina is gradually removed until the surgeon can see the nerves. The nerves are then gently moved slightly to expose the disc between two vertebrae.

Using various instruments, an annulotomy is preformed and the nucleus pulposus is removed through the right or left sides of the spinal canal. A first disc member is then inserted into the annulus followed by a second disc member, the discs are aligned and secured to each other. The annulotomy is repaired and the space formerly filled with the nucleus pulposus being then occupied by the endoprosthetic disc of the present disclosure.

In an aspect of the disclosure, assemblies of endoprosthetic discs may be preconstructed. To implant the endoprosthesis assembly, information is obtained regarding the patient's height, size, shape, and nature of a patient's damaged spine. Thereafter, one or more prosthetic disc units are selected to restore the correct height by determining the tension to achieve that height and the assemblies may be constructed in conformity with that information. In another aspect of the disclosure, the completed and conformed disc assembly is implanted in the patient's spine.

These and other features, objects and advantages of the disclosure will become apparent to those persons skilled in the art upon reading the details of the disclosure as more fully described below.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE DRAWINGS

Before the subject devices, systems and methods are described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

The present disclosure is directed to replacing the intervertebral disc, including the annulus and/or the nucleus, for treating or preventing further degeneration and/or herniation of the intervertebral disc by replacement. This is accomplished by implantation of one or more endoprosthetic discs of the present disclosure between one or more adjacent vertebral bodies.

Unless defined otherwise, all technical and scientific terms used herein have the same meaning as commonly understood by one of ordinary skill in the art to which this disclosure belongs. For example, the terms vertical and horizontal are used herein relative to a standing human being in the anatomical position. The terms "anterior", "posterior", "superior" and "inferior" are defined by their standard usage in anatomy; "anterior" refers to the region towards the front and the term "posterior" refers to the region towards the back. The term "sagittal" refers to regions on either side of the central midline axis of a standing human being; "superior" is upward toward the head; and "inferior" is lower or toward the feet. In the case of tools and apparatus, "distal" and "distally" are away from the body of the tool user and "proximal" and "proximally" are nearer or close to the body of the tool user.

The terms "upper" and "lower" are used herein to refer to the structure of the disc members as shown in the referenced drawings with respect to a reference position of the vertebrae on either side of the nucleus to be replaced. A "superior" vertebral body surface is the upper portion of a vertebral body onto which the spinal disc rests and an "inferior" vertebral body surface is the lower portion of a vertebra body positioned above the spinal disc of a functional spinal unit.

It will be appreciated that the focus of the disclosure is on those spinal discs found in the lumbar and lumbosacral regions of the spine; however, the disclosure here is not so limited and that adaptations and modifications can be made for use in the cervical spine and, much less frequently indicated, the thoracic spine.

Figure 1:
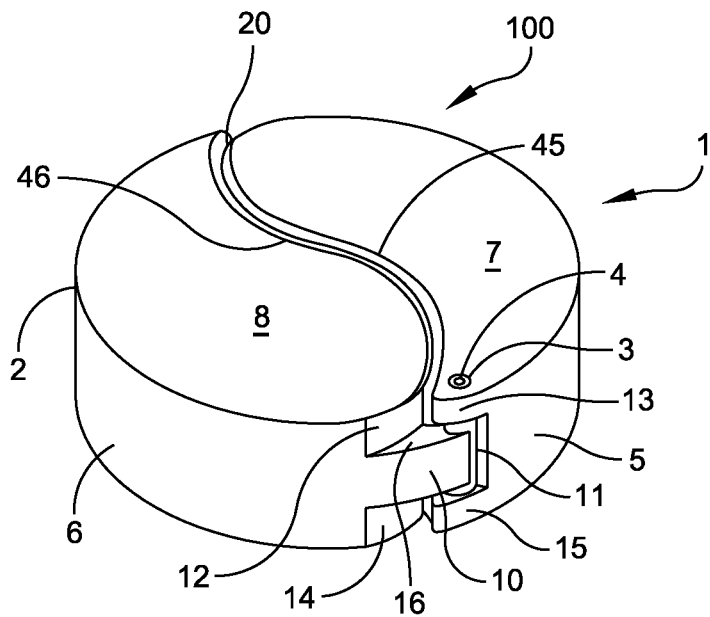
FIG. 1 shows a perspective view of an embodiment of an endoprosthetic disc of the present disclosure.

FIG. 1 shows one embodiment of endoprosthesis 100 comprising a pair of complimentary disc members 1 and 2 in alignment along a common boundary 20 defined on their upper surfaces by inner wall shoulders 45, 47 and 46, 48 to form a generally congruent structure having a discoid shape. First disc member 2 defines side wall 6 and upper surface 8. Second disc member 1 defines side wall 5 and upper surface 7. As shown in the drawing, disc members 1 and 2 each have a shape substantially similar to one-half of the familiar "yin-yang" symbol and when combined in proper alignment, will combine to form a disc-like shape comprising two more or less equal halves.

Positioned between and joining disc members 1 and 2 is a hinge structure formed by complimentary projections and recesses formed within the disc member bodies. In the embodiment shown, the hinge structure is generally formed by a projection or knuckle 10 defined by upper knuckle wall 12 having hinge upper and lower surfaces 16 and 18 (not shown) and lower knuckle wall surface 14. Knuckle 10 extends into hinge recess 11, the opening of which is defined by upper butt hinge 13 and lower butt hinge 15 which are in operative communication with upper and lower hinge surfaces, 16 and 18 respectively.

It will be appreciated that the hinge structure may be formed in any number of ways including but not limited to a conventional pin and barrel type of arrangement but by complimentary projection pins and detents which may be formed within the respective disc body members. In its simplest form, the disc body members are said to be hingedly connected and thus, the structures shown in FIG. 1 and all subsequent drawings are exemplary and not exhaustive. Other hinge arrangements are contemplated to be within the scope of the disclosure and the invention contemplated by the disclosure. The shape of disc members 1 and 2 may also be generally referred to as a "fat-comma", "twisted tear-drop" and/or "paisley" shape and each term can be generally understood to refer to the shape substantially disclosed by the drawings and may be used interchangeably herein without departing from the spirit and scope of the disclosure.

Although not shown in the FIG. 1, it will be understood that disc members 1 and 2 have corresponding identically configured lower surface structures (not shown) opposite upper surfaces 7 and 8. Upper surface structures 7 and 8 (and corresponding lower surfaces, not shown) may also be slightly convexed relative to common boundary 20 to form a relatively constant curvature away from the body of endoprosthesis 100 so as facilitate better placement and physical wear characteristics of endoprosthesis 100 within the intraspinal space. Also understood but not shown is that hinge connection shown by pin 4 in bore 3 will have a corresponding structure on the lower surface. In some embodiments pin 4 may extend completely through body members 1 and 2 with corresponding bore 3 located on upper and lower surfaces of member 1. In such embodiment, pin 4 will be situated substantially within body member 2 extending sufficiently to engage bore 3 on at least one surface of member 1 to form an operational hinge mechanism. It will also be appreciated that in alternative embodiments the hinge elements may be formed by a combination of raised pins formed within a hinge bearing surface member which may be engaged by detents or bores which may or may not extend through to the upper and lower surfaces of either member 1 or 2. It will likewise be appreciated that in still other types of embodiments, other types of hinge assembly elements may be employed and/or may be employed in combination with existing hinge elements located on either body member.

It will be understood that the endoprostheses of the present disclosure may be fabricated of metal, metal alloys, ceramics, plastics and combinations thereof. Particularly preferred metal alloys are orthopedic metal alloys specifically produced for the fabrication of artificial joints. These metal alloys have certain desirable characteristics, namely, strength, resilience and biocompatibility. Strength meaning that they will not break or permanently deform even under heavy constant loads; resilience meaning that they possess the requisite level of stiffness (e.g. too much stiffness will shield the spinal column too much from body weight); and, biocompatible meaning that they must be well tolerated by bone tissue.

Particularly useful orthopedic metal alloys include cobalt-chromium alloys, stainless steel alloys and titanium alloys all of which are well tolerated by bone tissue. Titanium alloys have particularly advantageous properties in that they have high strength, corrosion resistance and biocompatibility characteristics as compared to stainless steel and cobalt-chromium alloys.

Suitable plastics that may also be useful in the endoprostheses of the present disclosure may include medical-grade polyethylene commonly used on the surface of one implant that is configured to contact another implant. Polyethylene is very durable when it comes into contact with other materials. When a metal implant moves on a polyethylene surface, as it does, for example, in many joint replacements, the contact is very smooth and the amount of wear is minimal.

Figure 2:
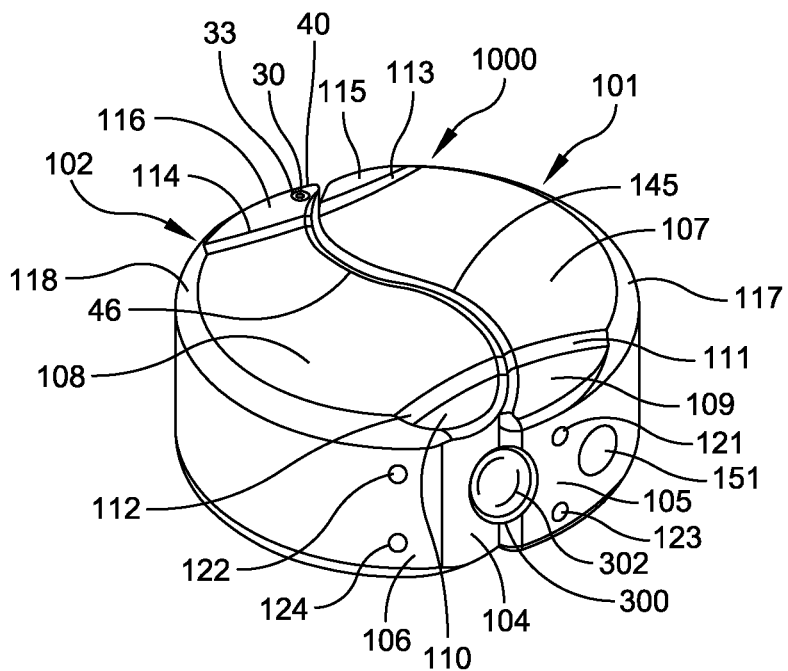
FIG. 2 shows a perspective view of an alternate embodiment of an endoprosthetic disc of the present disclosure.

FIG. 2 shows an embodiment of endoprosthesis 1000 of the present disclosure. Endoprosthesis 1000 comprises a pair of complimentary disc members 101 and 102 substantially identical on their upper and lower surfaces and which are in alignment along a common lateral boundary 200 defined on their upper and lower surfaces by inner wall shoulders 145, 147 and 146, 148 to form a generally congruent structure having a discoid shape.

As shown in FIG. 2, disc members 101 and 102 each have surface shapes substantially similar to one-half of the familiar "yin-yang" symbol and when combined in proper alignment, will combine to form a disc-like shape comprising two more or less equal halves. With reference to FIG. 2 the shape of disc members 101 and 102 may also be generally referred to as a "fat-comma", "twisted tear-drop" and/or "paisley" shape and each term will be understood to refer to the shape substantially disclosed by FIG. 2 and may likewise be used interchangeably herein without departing from the spirit and scope of the disclosure. For reference purposes, the wider end portions of the first and second disc members may generally be referred to as the "head" or leading edge with the narrower end being referred to as the "tail" or trailing edge.

It will be also appreciated that with respect to embodiments disclosed in FIG. 2, first disc member 102 and second disc member 101 are designated as such with respect to one relative order of insertion and positioning of first and second disc members 102 and 101 and is not intended to be absolute designation of any particular order or sequence except for referential purposes with respect to the figures. It will likewise be appreciated that second disc member 101 can be inserted first with first disc member 102 being inserted second and vice versa.

First disc member 102 defines first disc member leading edge wall 104, first disc member outer side wall 106 and first disc member upper surface 108. Positioned above first disc member leading edge wall 104 is first disc member upper surface leading edge 110 and first disc member upper surface leading edge transition zone 112. First disc member upper surface leading edge transition zone 112 is positioned between and separates first disc member upper surface 108 from first disc member upper surface trailing edge transition zone 114 and first disc member upper surface trailing edge 116. As shown in FIG. 2, transition zones 112 and 114 are positioned on either side of first disc member upper surface 108. The transition zones generally define regions on upper surface 108 where the relative height of the upper surface diminishes to a slightly lower height (and therefore overall "thickness") as further defined by first disc member upper surface leading edge 110 and first disc member upper surface trailing edge 116. The relative positions of transition zones 112 and 114 are not absolute and in some embodiments may be moved forward or backwards relative to the positions shown in FIG. 2.

Positioned adjacent first disc member upper surface 108 is first disc member upper surface shoulder 118. Upper surface shoulder 118 may be a smooth rounded surface to improve overall fit and wear characteristics of endoprosthesis 1000 and may be configured differently in other embodiments. For example, in other embodiments situated generally below upper surface shoulder 118 on first disc member outer side wall 106 is a side wall notch may be defined. The side wall notch may be a groove or depression adapted for receiving one embodiment of surgical tool or other apparatus for stabilizing front disc member 102 during insertion into the spinal space. As shown in FIG. 2, located generally within stabilizing first disc member outer side wall 106 is at least one first disc member wire channel 122. In other embodiments, a second first disc member wire channel may optionally be present.

Second disc member 101 defines, second disc member outer side wall 105 and second disc member upper surface 107. Positioned distally on second disc member leading outer side wall 105 is second disc member leading edge (not shown) above which is second disc member upper surface leading edge 115 and second disc member upper surface leading edge transition zone 113. Second disc member upper surface leading edge transition zone 113 is positioned between and separates second disc member upper surface 107 from second disc member upper surface trailing edge transition zone 111 and second disc member upper surface trailing edge 109. As shown in FIG. 2, second disc member transition zones 111 and 113 are positioned on either side of second disc member upper surface 107. As in the case of first disc member 102, second disc member transition zones 111 and 113 generally define regions on upper surface 107 where the relative height of the upper surface diminishes to a slightly lower height (and therefore overall "thickness") as further defined by second disc member upper surface leading edge 115 and second disc member upper surface trailing edge 109. The relative positions of second disc member transition zones 111 and 115 are not absolute and in some embodiments may be moved forward or backwards relative to the positions shown.

Positioned adjacent second disc member upper surface 107 is second disc member upper surface shoulder 117. Upper surface shoulder 117 may be a smooth rounded surface to improve overall fit and wear characteristics of endoprosthesis 1000 and may be configured differently in other embodiments. Situated generally below second disc member trailing edge on second disc member outer side wall 105 is stiffening rod bore 151. Stiffening rod bore 151 is a channel or bore adapted for receiving one embodiment of surgical tool or other apparatus for delivering the first and second disc members 101 and 102 to a desired location intradiscally.

Positioned rearwardly on endoprosthesis 1000 is the hinge assembly with upper butt hinge 33 shown having bore 30 and pin 40. Although not shown on FIG. 2, it will be appreciated that the reverse side of endoprosthesis 1000 will have corresponding and complimentary structures relating to or functionally equivalent to upper butt hinge 33, bore 30 and pin 40 to form operative hinge mechanism. It will also be appreciated that the complimentary imaged sections are operatively joined to one another at their respective head and tail ends via a hinge and/or other flexible connection which facilitates articulation about an axis. As used herein, hinge may include other live articulations including but not limited to ball-and-socket assemblies, springs, swivels, flexible joints, universal joints, pivot assemblies and their mechanical equivalents. In this manner, body members 101 and 102 are said to be operatively joined or hingedly connected to one another. Two remaining numbered structures and elements illustrated in FIG. 2 are discussed below in the detailed description of the Figures which follow.

Referring proximally in FIG. 2, in the forward portion of the drawing is tool shaft bore 300 and stiffening rod bore 151. Tool shaft bore is formed within the inner surfaces of body members 101 and 102 each of which carry at least, in part, a U shaped channel that forms a generally hollow pathway or conduit when the body members are rotated into each other to form the complete discoid shape. Stiffening rod bore 151 supports the body member segments during insertion and placement into a spinal space via an associated insertion tool (not shown). Adjacent stiffening rod bore 151 are second disc member wire channel 121 and optionally wire channel 123.

As will be seen, wire channel 121 and 123 are in operative communication with wire channels 122 and 124 of first disc member and together with a wire, act to form pulley like mechanism operatively engaging and closing the body members via an insertion tool.

Not shown in the FIG. 2, disc members 101 and 102 have corresponding identically configured lower surfaces (not shown) opposite upper surfaces 107 and 108. Upper surfaces 107 and 108 (and corresponding lower surfaces, not shown) may also be slightly convexed relative to the cross section of endoprosthesis 1000 to form a relatively constant curvature away from the body of endoprosthesis 1000 so as facilitate better placement and physical wear characteristics of endoprosthesis 1000 within the intraspinal space.

Figure 3:
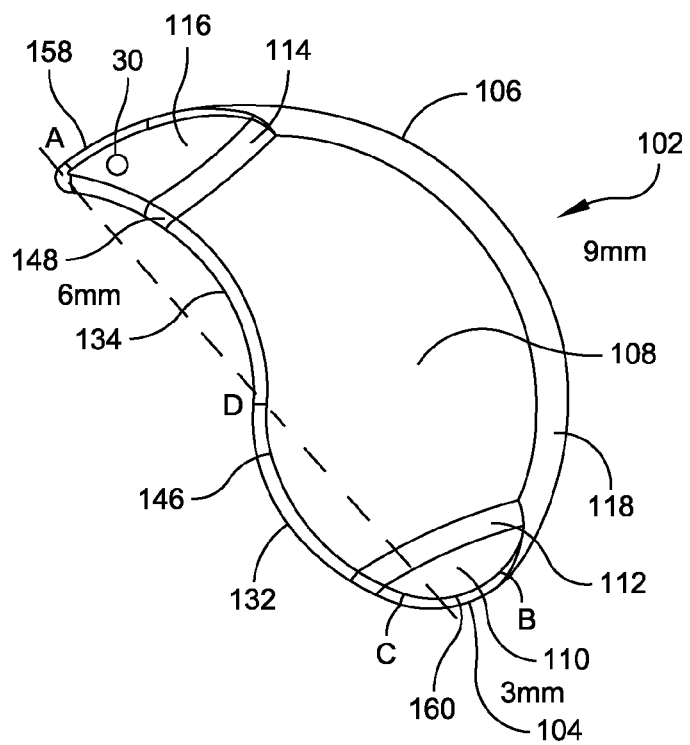
FIG. 3 shows a top view of a first disc segment of the embodiment shown in FIG. 2.

Referring now to FIG. 3, there is shown a top plan view of first disc member 102. As may be appreciated from the drawing, first disc member has a shape substantially similar to one-half of the "yin-yang" symbol generally defined a continuous upper and lower periphery and further defined by outer wall shoulder 118, leading edge shoulder 160, convex inner wall shoulder 146, concave inner wall shoulder 148 and trailing edge shoulder 158.

Outer wall 106 may be generally defined as a semi-circular arc having a relatively constant radius of curvature defined by the line A-B. Contiguous with outer wall 106 is leading edge wall 104 having a radius of curvature less than outer wall 106. Leading edge wall 104 may be generally defined by the line B-C. Contiguous with leading edge wall 104 is inner wall convex wall 132 having a radius of curvature that may be generally defined by line C-D. Contiguous with inner convex wall 104 is inner concave wall 134 which in turn is more or less contiguous on the end opposite inner convex wall 132 with outer wall 106 and is generally defined by the line D-A. Inner convex wall 132 and inner concave wall 134 will generally have similar radii of curvature in opposite directions, which is to say that inner convex wall 132 will extend away from the body of first disc member 102 while inner concave wall will extend towards the body of first disc member 102. For example, in an embodiment, outer wall 106 may have a radius of curvature of approximately 9 mm, leading edge wall may have a radius of curvature of about 3 mm and inner convex and inner concave walls may each have a radius of curvature roughly 6 mm. It will also be appreciated that the peripheral wall of first disc member may further define additional areas having a smaller radius of curvature at or near point A, for example, to create a more rounded tail portion end of the one-half "yin-yang" shape.

FIG. 3 shows first disc member upper surface 108 more or less situated centrally on the upper surface of first disc member 102. Generally positioned between first disc member upper surface 108 and outer wall 106 is shoulder 118. In the embodiment shown shoulder 118 may be a generally uniform rounded edge to facilitate fit and wear of the endoprosthesis of the present disclosure when inserted intradiscally; however, it will also be appreciated that the shoulder 118 may be optionally absent or non-uniform in its configuration and may take other forms with a greater or lesser rounded edge surface. Positioned towards the head portion of first disc member 102 are first disc member upper surface leading edge 110 and first disc member upper surface leading edge transition zone 112. First disc member upper surface leading edge transition zone 112 is positioned between first disc member upper surface 108 and first disc member leading edge surface. Positioned posteriorly on the first disc member upper surface 108 towards the tail end of first disc member 102 are upper surface trailing edge transition zone 114 and first disc member upper surface trailing edge 116. Also positioned at or near trailing edge 116 is bore 30.

In the embodiment shown bore 30 is adapted to receive a pin or other semi rigid insert to complete and form a hinge assembly with a complimentary body member. It will be appreciated that a hinge assembly may also be formed without employing a bore and pin arrangement and bore 30 may also generally signify an axis point about which the body members may rotate with respect to one another. On the peripheral wall opposite shoulder 108 is inner shoulder 146 which may extend more or less from the upper leading edge surface 110 to upper leading trailing edge surface 116.

As will be appreciated by the figures transition zones 112 and 114 are positioned on either side of first disc member upper surface 108. The transition zones generally define regions on upper surface 108 where the relative height of the upper surface diminishes to a slightly lower height (and therefore overall "thickness" in cross section) as further defined by first disc member upper surface leading edge 110 and first disc member upper surface trailing edge 116. The relative positions of transition zones 112 and 114 are not absolute and in some embodiments may be moved forward or backwards relative to the positions shown in FIG. 3. It will likewise be appreciated that the lower surfaces (not shown) of first disc member 102 will be substantially identical in form and function to the structures and reference points generally described with respect to the upper surfaces and peripheral walls.

Figure 4:
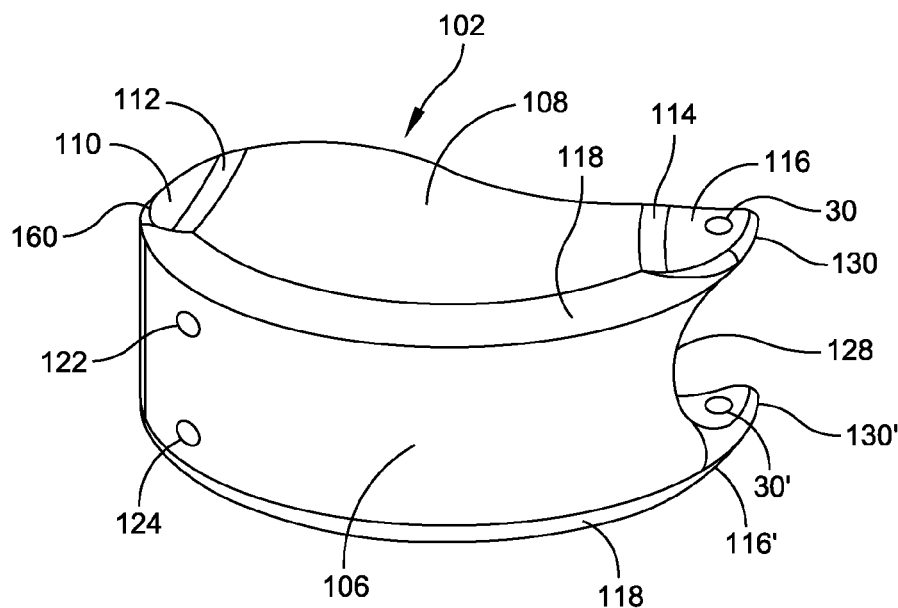
FIG. 4 shows an outer side perspective view of the first disc segment of the embodiment shown in FIG. 3.

FIG. 4 is an outer side perspective view of an embodiment of the first disc member of FIG. 2. Situated generally below upper surface shoulder 118 is first disc member outer side wall 106. Side wall 106 may optionally define a groove or depression (not shown) adapted for receiving one embodiment of surgical tool or other apparatus for stabilizing first disc member 102 during insertion into the annulus of a spinal disc. Side wall 106 may also define other stabilizing elements such as an orifice or a series of orifices which into which may be received a surgical tool or other similar device to aide in stabilizing or positioning the member. Located generally within side wall 106 are first disc member first wire channel 122 and, optionally, first disc member second wire channel 124. It will be understood that the wire channels are bores forming passageways that extend from the outer surface of the disc member through the disc member to the inner surface of the disc member. The outer surface numeral designations will appear as whole numbers whereas the inner surface designations will appear as the corresponding number with the "'" designation (i.e., 122', 124'). In other embodiments, a side wall groove may be present and first and second suture channels may be optionally positioned directly within the groove side wall.

Referring generally towards the tail portion of FIG. 4, it will be seen that a pair of upper and lower butt hinges 130 and 130' are formed within the first body member generally at or near the upper and lower trailing edge surfaces 116 and 116'. Upper and lower butt hinges 130 and 130' are configured to receive the knuckle portion of second body member as will be discussed in detail below. Upper and lower butt hinges further define bores 30 and 30' adapted to receive a pin or other rigid member which securely joins the first and second body members and which provides a pivot axis of a hinge. Situated between upper and lower butt hinges 130 and 130' is side wall notch tail for facilitating partial rotation of the second disc member about the axis point of the hinge. As will be appreciated from FIG. 4 and well as FIGS. 5 and 6, discussed more fully below, the upper and lower surfaces of first disc member 102 are essentially mirror images, which is to say that the structures, surfaces and proportions of the upper and lower portions of the first disc segment are identical as measured by a longitudinal cross sectional line positioned through its central axis.

Figure 5:
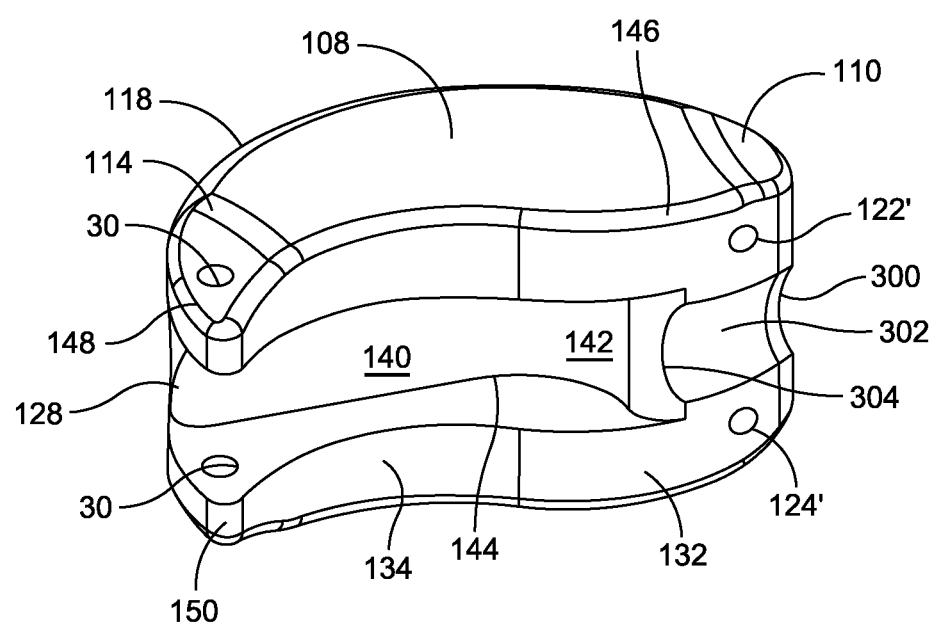
FIG. 5 is an inner side perspective view of the first disc segment of the embodiment shown in FIG. 3.

FIG. 5 is an inner wall perspective view of the first disc member shown in FIG. 4. First disc member upper surface 108 is shown having first disc member upper leading edge surface 110 towards the head portion and first disc member trailing edge surface 116 towards the tail portion of first disc member 102. Positioned on the inner peripheral edge of first disc member 102 are inner wall shoulders 146 and 148 defining in general, a continuous boundary between upper surface 108 and inner convex wall 132 and between upper surface 108 and inner concave wall 134. Inner shoulder 146 may extend more or less from the upper leading edge surface 110 to upper trailing edge surface 116 at tail wall 150. Positioned adjacent inner shoulder 146 on upper trailing edge surface is the continuation of inner concave wall shoulder 148 which extend on the periphery until it transitions into outer shoulder 118.

Situated within inner convex wall 132 and inner concave wall 134 is inner notch 140 defined on one end by inner notch convex end 142 and by side wall notch tail 128 on its opposite end. Inner notch 140 is further defined by inner notch floor 130 and inner notch ceiling 136. Located within inner notch convex end 142 is a generally "U" shaped tool support channel 302 defined by opening 300 at one end and inner conduit channel 304 at the other end. Tool support channel 302 is adapted to mateably receive an insertion and assembly tool as will be discussed in the figures below. In other embodiments, tool support channel 302 may be repositioned or may be absent. Positioned on either side of tool support channel 302 and roughly positioned on either side of inner convex wall 132 are first suture channel 122' and first member second suture channel 124'. As used herein the "'" designation will refer to the corresponding suture channel orifice on the inner wall of first disc member 102.

Figure 6:
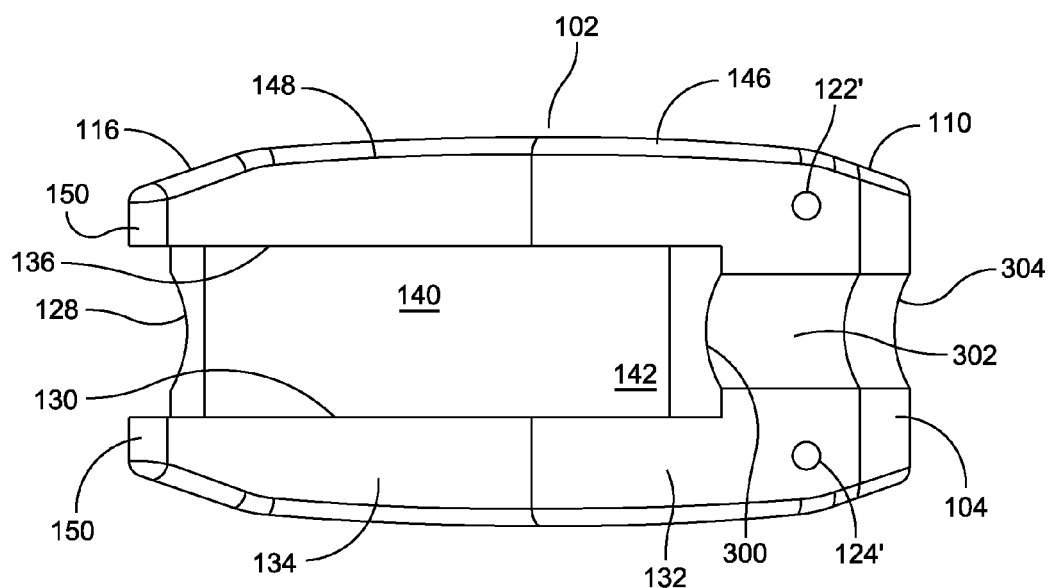
FIG. 6 is an inner side view of the first disc segment of the embodiment shown in FIG. 3.

FIG. 6. is a side perspective view of first disc member 102 as shown in FIGS. 4 and 5. The slightly convexed shape of first disc member may be seen with respect to the mirror imaged upper surfaces identified in FIGS. 2 through 5 and the lower surfaces. Inner wall shoulders 146 and 148 respectively define a continuous boundary between upper surface 108 and inner convex wall 132 and between upper surface 108 and inner concave wall 134. Inner shoulder 146 and 148 may extend more or less from the upper leading edge surface 110 to upper trailing edge surface 116 at tail wall 150.

Inner notch 140 is defined on one end by inner notch convex end 142 and by side wall notch tail 128 on its opposite end. Inner notch 140 is further defined by inner notch floor 130 and inner notch ceiling 132. It will be appreciated however that the terms floor and ceiling are for reference purposes with respect to their positions shown in FIG. 6 inasmuch as the figure and the first disc member itself may be rotated 180° in which case the floor becomes the ceiling and vice versa.

Located within inner notch convex end 142 is tool support channel 302 defined by tool support opening 300 and tool support conduit end 304 of first disc segment 102. Tool support channel may be disposed generally mid line with respect to the upper and lower surfaces of the first disc segment 102. It will be appreciated that all of the tool support channel elements 300, 302 and 304 are generally "U-shaped" and which together with corresponding elements discussed below on a second body member, will form a generally round or ovoid conduit for supporting and positioning a formed discoid within the spinal space. In the embodiment shown in FIG. 6, first member first channels 122' and 124' are located on the peripheral edge of inner convex sidewall 132.

Figure 7:
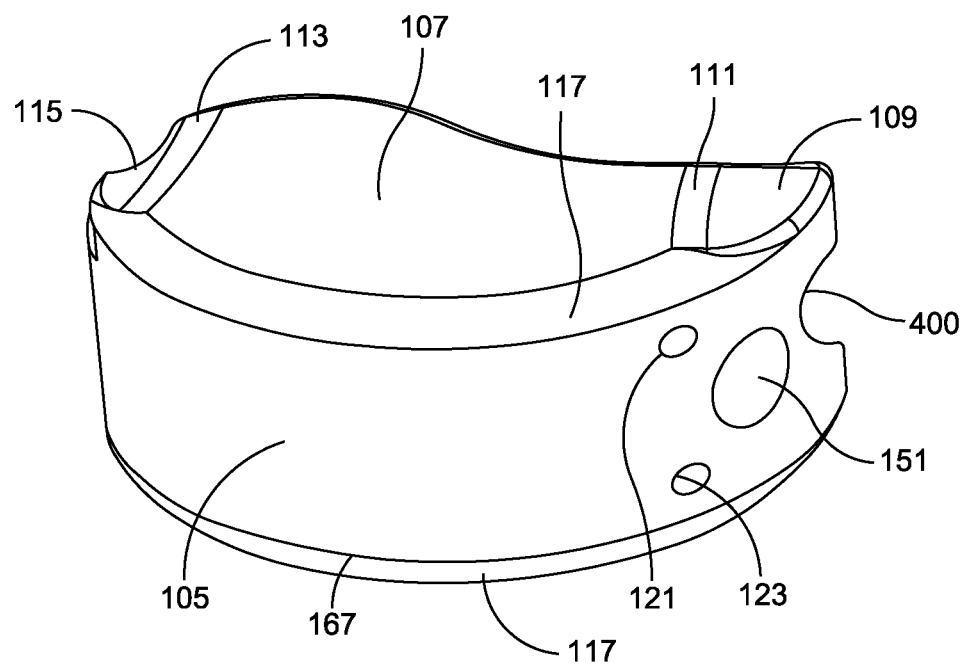
FIG. 7 is an outer side perspective view of an embodiment of a second disc segment shown in FIG. 2.

FIG. 7 is an outer side perspective view of an embodiment of the second disc member of FIG. 2. Second disc member upper surface 107 is more or less situated centrally on the upper surface of second disc member 101. Generally positioned between second disc member upper surface 107 and outer wall 105 is shoulder 117. In the embodiment shown shoulder 117 may be a generally uniform rounded edge to facilitate fit and wear of the endoprosthesis of the present disclosure when inserted intradiscally; however, it will also be appreciated that the shoulder 117 may be optionally absent or non-uniform in its configuration and may take other forms with a greater or lesser rounded edge surface. Positioned towards the head portion of second disc member 101 is second disc member upper surface leading edge 115 and second disc member upper surface leading edge transition zone 113. Second disc member upper surface leading edge transition zone 113 is positioned between second disc member upper surface 107 and second disc member leading edge surface 115.

In the embodiment shown second disc member leading edge surface 115 has a slightly concaved curvature which is adapted to accommodate the rotational movement of a first disc member with which it may be mechanically or otherwise linked. Positioned posteriorly on the second disc member upper surface 107 towards the tail end of second disc member 101 is upper surface trailing edge transition zone 111 and second disc member upper surface trailing edge 109. On the peripheral wall opposite shoulder 107 is inner shoulder 145 which may extend more or less from the upper leading edge surface 115 to upper leading trailing edge surface 109.

As will be appreciated from the figures, transition zones 111 and 113 are positioned on either side of second disc member upper surface 107. The transition zones generally define regions on second member upper surface 107 where the relative height of the upper surface diminishes to a slightly lower height (and therefore overall "thickness" in cross section) as further defined by second disc member upper surface leading edge 115 and second disc member upper surface trailing edge 109. As in the case of first disc member 102, the relative positions of transition zones 111 and 113 are not absolute and in some embodiments may be moved forward or backwards relative to the positions shown in FIG. 7; however it will understood that the relative positions of the transition zones of the second disc member will generally correspond to the placement of the transition zones on a first disc member. It will likewise be appreciated that the lower surfaces (not shown) of second disc member 101 will be substantially identical in form and function to the structures and reference points generally described with respect to the upper surfaces and peripheral walls.

Situated generally below upper surface shoulder 117 and within second disc member outer side wall 105 is stiffening rod bore 151. Stiffening rod bore is preferably cavity or chamber adapted for receiving a portion of one embodiment of surgical tool or other apparatus for delivering the first and second disc members to a desired position within the annulus of a spinal disc. Stiffening rod bore 151 may also take other forms such as a groove, slot or a series of orifices which into which may be received a surgical tool or other similar device to aide in delivering and positioning the first and second disc members. Located generally within second member side wall 105 are second disc member first suture channel 121 and optional second disc member second suture channel 123. Positioned rearwardly of stiffening rod bore 151 is tool support Notch 400. It will be understood that tool support notch forms the complimentary section of the combined tool support conduit within tool support opening 300 of first disc member 102.

Figure 8:
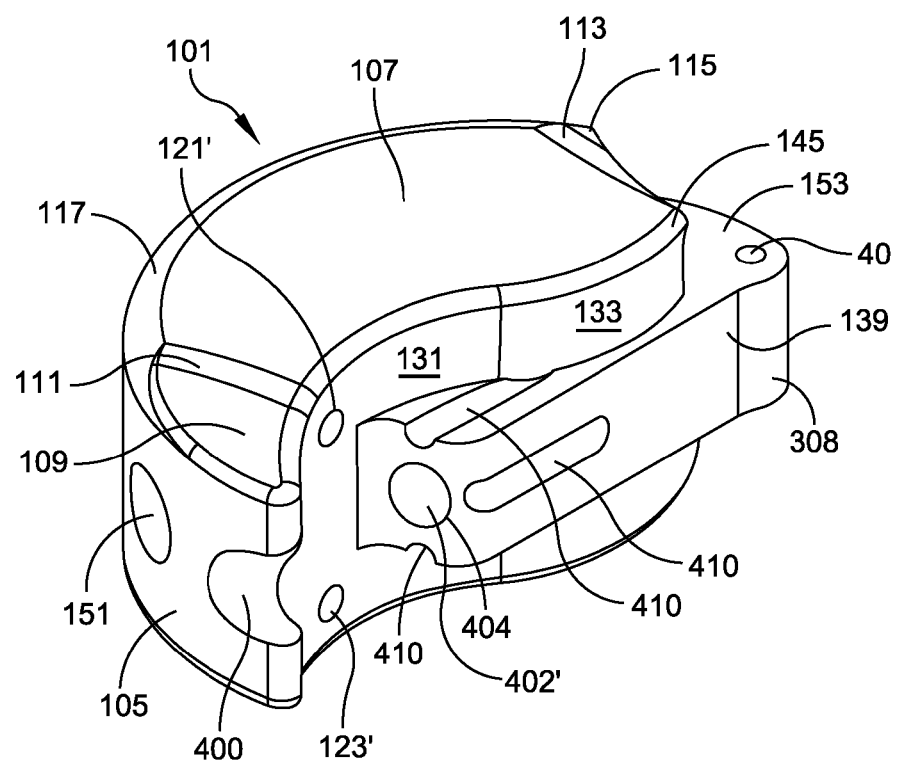
FIG. 8 is an inner side perspective view of an embodiment of the second disc segment shown in FIG. 7.

FIG. 8 is an inner wall perspective view of the second disc member shown in FIG. 7. Second disc member upper surface 107 is shown having a partially truncated second disc member upper leading edge surface 115 towards the head portion and second disc member trailing edge surface 109 towards the tail portion of second disc member 101. Positioned on the inner peripheral edge of second disc member 101. The shape of leading edge surface 115 is adapted to facilitate rotation of the first and second body members relative to each other about an axis point generally defined by pin bore 50 which is mateably recessed by bore 30 in first disc member 102. Positioned on the inner peripheral edge of second disc member 101 are inner wall shoulders 145 and 147 defining in general, a continuous boundary between upper surface 107 and second disc member inner convex wall 133 and between upper surface 107 and inner concave wall 131. Inner shoulders 145 and 147 may extend more or less from partially truncated second disc member upper leading edge surface 115 to upper trailing edge surface 109 at second disc member tail wall 161. Positioned adjacent inner convex wall shoulder 145 on upper trailing edge surface is inner concave well shoulder 147 which extend on the periphery until it transitions into outer shoulder 117.

Situated within inner convex wall 132 and inner concave wall 134 is boss 139 defined on one end by inner notch concave end 141 and by second disc member side wall notch tail 157 on its opposite end. Inner notch 140 is further defined by boss floor 153 and boss ceiling (not shown). Situated on boss 139 are stabilizing grooves 410 for stabilizing an insertion and assembly tool. The number and configuration of the stabilizing grooves may vary according to the tool design and it will be appreciated that these are design preferences, not absolutes. Additionally, stabilizing grooves 410 may also serve as detents for corresponding protrusions positioned on the inner surface of the first disc segment member. Also disposed within boss 139 are boss conduit opening 406 and tool support conduit 402 which extends the length of boss 139 with a corresponding opening (not shown) generally located at or near hinge knuckle 308. The tool support conduit begins at tool conduit opening 400 and traverses the second member body via boss conduit opening 404 through tool support conduit 402 exiting at the rearward or distal end of the second member body. Positioned on either side are first suture channel 121' and optional second member second suture channel 123'. As in the case of first disc member 102, first and second suture channels are bores having passageways with outer wall openings and inner wall openings. The inner openings are identified using the "'" designations, (i.e., 121' and 123') whereas corresponding outer openings are identified without the designation (i.e., 121 and 123).

Figure 9:
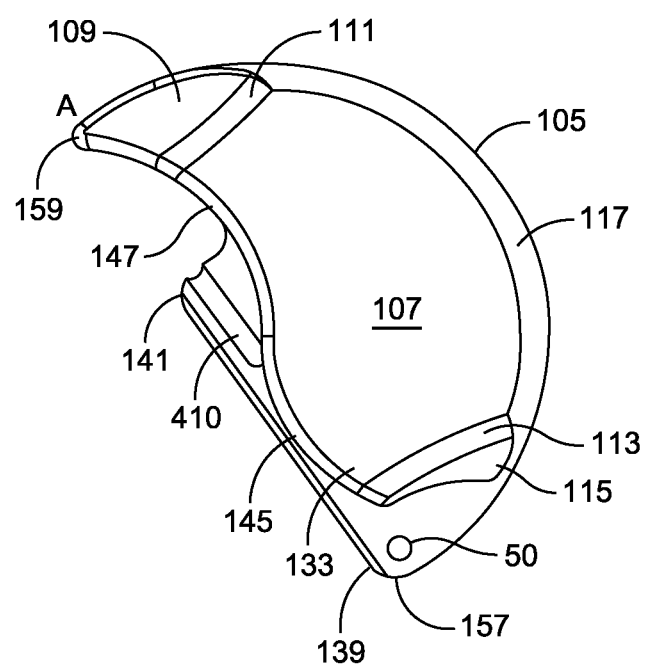
FIG. 9 is a top view of a second disc segment of the embodiment shown in FIG. 7

Referring now to FIG. 9, there is shown a top plan view of second disc member 101 shown in FIGS. 7 and 8. Second disc member 101 define upper and lower surface shapes substantially similar to one-half of the "yin-yang" symbol generally defined by a continuous upper and lower periphery and further defined by outer wall shoulder 117, leading edge shoulder 125, convex inner wall shoulder 145, concave inner wall shoulder 147 and trailing edge shoulder 159.

Outer wall 105 of second disc member 101 may be generally defined as a semi-circular arc having a relatively constant radius of curvature defined by the line A-B. Contiguous with outer wall 105 is leading edge wall 125 having a radius of curvature less than outer wall 105. Leading edge wall 125 may be generally defined by the line B-C. Contiguous with leading edge wall 125 is inner convex wall 133 having a radius of curvature that may be generally defined by line C-D. Contiguous with inner convex wall 133 is inner concave wall 131 which in turn is more or less contiguous on the end opposite inner convex wall 133 with outer wall 105 and is generally defined by the line D-A. Inner convex wall 133 and inner concave wall 131 may preferably have similar radii of curvature in opposite directions, which is to say that inner convex wall 133 will extend away from the body of second disc member 101 while inner concave wall will extend inwardly towards the body of second disc member 101. For example, in an embodiment, outer wall 105 may have a radius of curvature of approximately 9 mm, leading edge wall may have a radius of curvature of about 3 mm and inner convex and inner concave walls may each have a radius of curvature roughly 6 mm. It will also be appreciated that the peripheral wall of second disc member may further define additional areas having a smaller radius of curvature at or near point A, for example, to create a more rounded tail portion end of the one-half "yin-yang" shape.

Second disc member upper surface 107 is shown having second disc member upper leading edge surface 115 towards the head portion and second disc member trailing edge surface 109 towards the tail portion of second disc member 101. As can be seen more clearly in FIG. 9, upper leading edge surface 115 and corresponding lower leading edge surface (not shown) are configured so as to permit the relational movement of the first disc member at pin bore 50. Positioned on the inner peripheral edge of second disc member 101 is convex inner wall shoulder 145 and concave inner wall shoulder 147 defining in general, a continuous boundary between upper surface 107 and second disc member inner convex wall 133 and between upper surface 107 and inner concave wall 131. Convex inner shoulder 145 and adjacent concave inner wall shoulder 147 may extend more or less from second disc member upper leading edge surface 115 to upper trailing edge surface 109 at second disc member tail wall 161. Positioned adjacent concave inner shoulder 147 on upper trailing edge surface is trailing edge shoulder 159 which extends on the periphery of the tail portion of second disc member 101 until it transitions into outer shoulder 117.

Situated of the surface of inner convex wall 133 and inner concave wall 131 and integrally formed therein is boss 139 defined on one end by second disc inner notch concave end 141 and by second disc member side wall notch tail 157 on its opposite end. Boss 139 is further defined by boss floor 153 on one surface and boss ceiling (not shown) on the opposite surface thereof. It will be understood that boss 139 is shaped to be mateably received by and fit substantially completely within inner notch 140 of first disc member 102 as shown in FIGS. 5 and 6. In other embodiments, boss 139 may be larger or smaller or configured as a tab or series of tabs which may be received partially or completely within corresponding orifices situated on a complimentary disc member to form a congruent discoid structure. Conversely, stabilizing grooves 410 may be configured to accept tabs or protrusions on a complimentary disc member.

Figure 10:
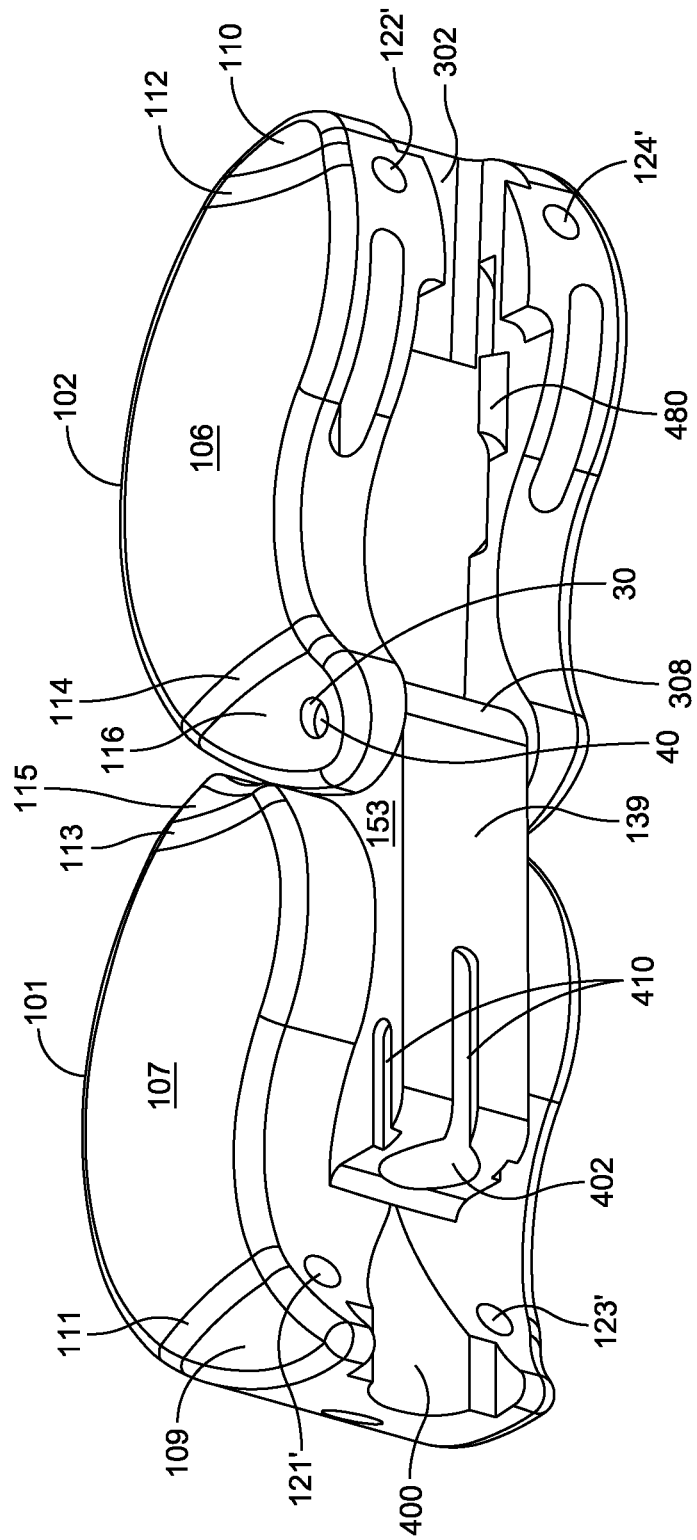
FIG. 10 shows a perspective view of an embodiment of the first and second disc segments of FIGS. 2-9 hingedly engaged in the open position.

FIG. 10 shows a side perspective view of a first and second disc segment assembly hingedly connected in the open configuration. Generally centrally situated with respect to the combined segments is the hinge assembly formed by bore 30 on the trailing edge surface 116 of first disc member 108 and pin 40 positioned in hinge knuckle 308 of second disc segment member 101. As can be seen from the drawing in FIG. 10, first disc member 102 and second disc member 101 define the within referenced physical and landmark structures previously called-out in FIGS. 2-9. For sake of brevity, the description and function of the various structures and landmarks will not be recited and are incorporated by reference. It will however be appreciated from FIG. 10 how disc segment members 101 and 102 are cooperatively engaged to form a unified segment assembly which may be inserted into a spinal space as a single unit. It will likewise be appreciated that leading edge 115 of second disc segment 101 is configured to permit the pivoting rotation of the first disc member about the axis generally defined by the hinge assembly.

Figure 11:
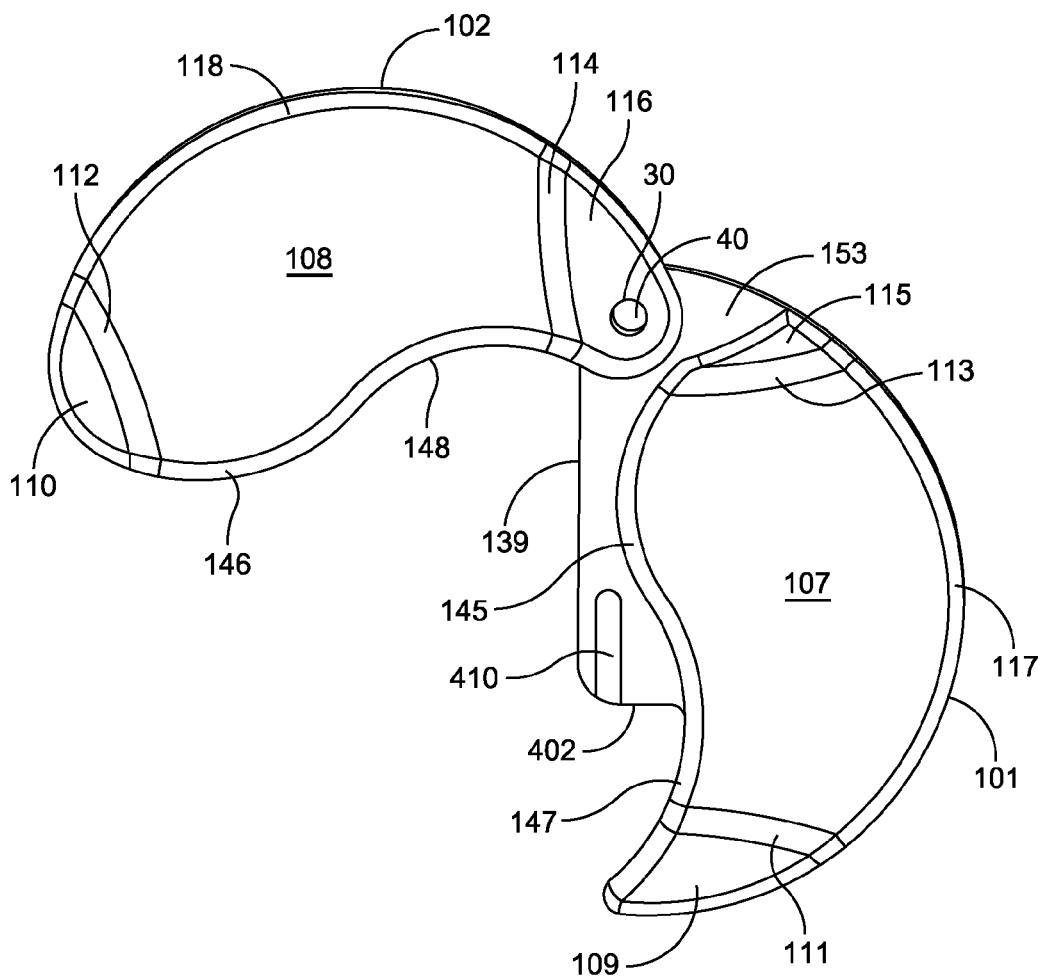
FIG. 11 is a top plan view of the first and second disc segments of the embodiment shown in FIG. 10 in partial closure.
Figure 12:
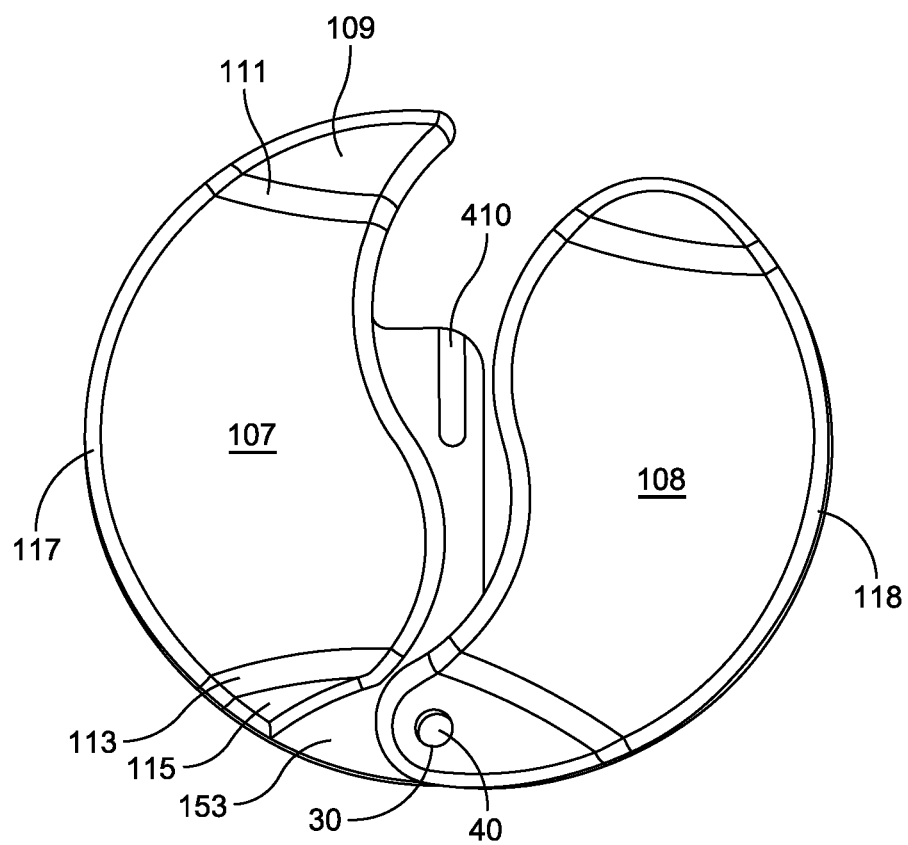
FIG. 12 is a top plan view of the first and second disc segments of the embodiment shown in FIG. 11 nearer complete closure.

FIGS. 11 and 12 show top plan views of the first and second disc segment assembly of FIG. 10 during stages of the closure process. It will be understood that as the first and second disc segment members are rotated towards one another at the pivot point they will be brought into contact along the shared interior wall surfaces. It will also be understood that as the disc segments are joined to form the discoid assembly, boss 139 will fit securely within the interior notch (not shown) of first disc segment member 108. In some embodiments, boss 139 may carry optional tabs, protrusions or projections that compressively fit within corresponding bores, grooves or orifices in the first disc segment member for securely fastening the first and second disc segment to one another. In still other embodiments, optional tabs, protrusions or projections and corresponding bores, grooves or orifices may be positioned on opposite disc member segments or may still further be arranged in any number of different combinations on the interior wall surfaces to provide compressive fitment of the first and second disc segment members. It will be appreciated that in some embodiments it may be desirable to remove or replace the discoid assembly after insertion into the spinal space and in still other embodiments the discoid assembly may define unlocking mechanisms to release the compressive fitment and disassemble the unified assembly.

Figure 13:
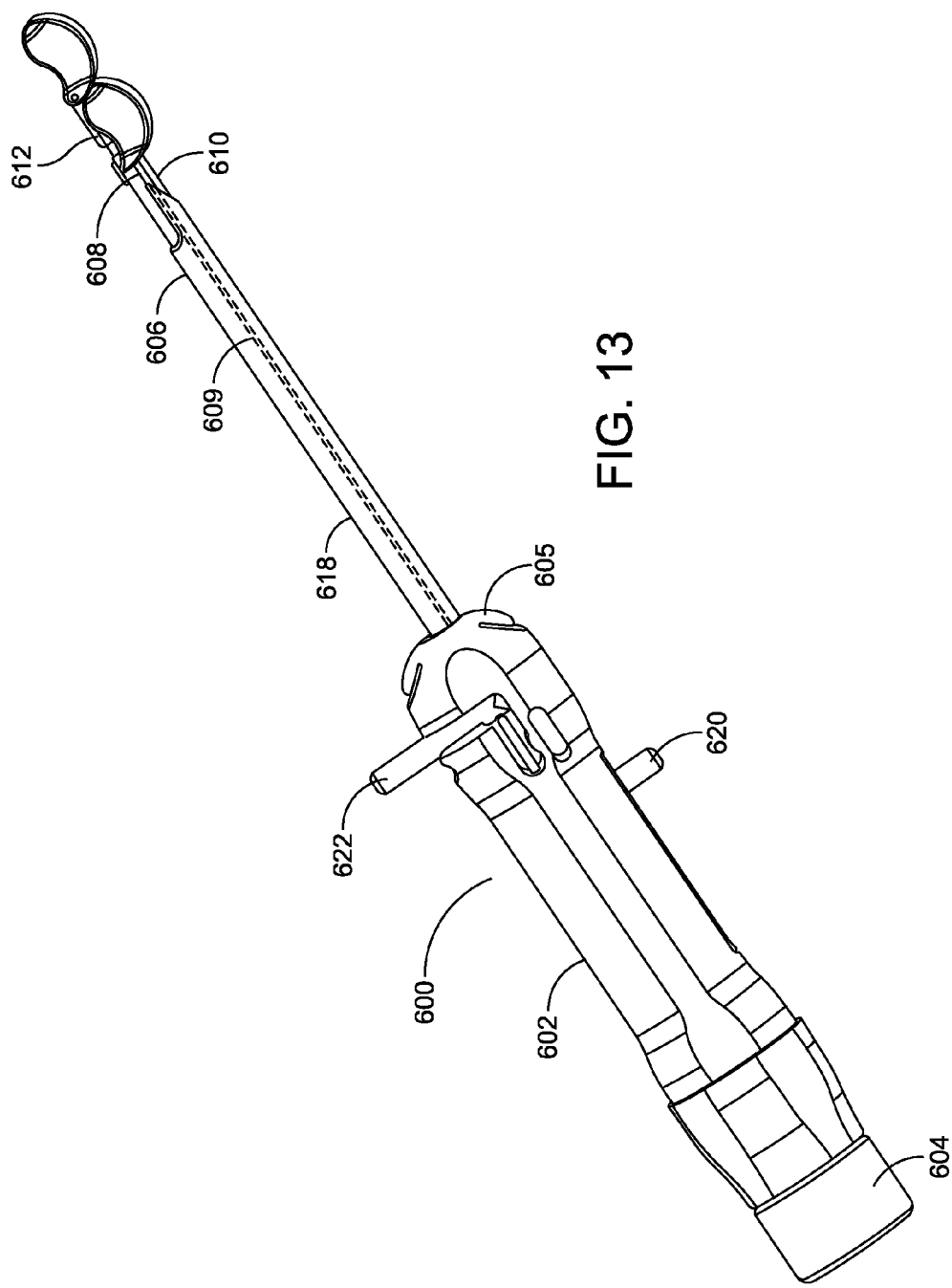
FIG. 13 shows a representative insertion tool having one embodiment of the first and second disc segments mounted thereon.

FIG. 13 is shows one embodiment of an insertion tool 600 generally having tool handle 602 for holding the tool and preferably a pair of parallel shaft housings 606 and 609 for insertion of the first and second disc segment members 102 and 101 within the intra spinal space. Handle 602 defines proximal end 604 and shaft end 605. Positioned on shaft end 605 is a shaft flange for securing stiffening rod shaft housing 609 and insertion shaft housing 606 into handle 602. In the embodiment shown insertion shaft housing 606 and rod shaft housing 609 and are arranged in substantially parallel fashion and may be annealed or fixedly attached to one another so as to form a substantially unitary structure, while in other embodiments the shaft housings may be separate but are preferably arranged in parallel alignment.

Situated within insertion shaft housing 606 is insertion shaft 610 having at its distal end shaft tip 612 for securing at least one of the first and second segment members. Securing means typically employed can define threaded mounts, compressive fitments, frangible connectors and other similar selectively detachable connection devices and methods. Shaft housings 606 and 609 may further define at least one closure wire 618 operatively connected to first and second disc segment members shown positioned. In the embodiment shown, adjacent shaft 610 is stiffening rod 608 for securely aligning the first and second disc segment members.

Positioned within or on handle 602 is tensioner 620. Tensioner 620 is operatively connected to a wire or cable in communication with one or more orifices of first and second disc segment members. Tensioner 620 may provide withdrawing tension on of a portion of the suture wire or suture cable and facilitate rotation of the first disc segment member 102 and the second disc segment member 101 towards one another and also facilitate disengagement of the discoid assembly from the tool head 612. Tensioner 620 may further define mechanisms for manipulating cables or wires that may be placed within the first and second disc segment member suture channels as generally disclosed herein. Tensioner 620 may take the form of any one of knobs, levers, ratcheted wheels and trigger mechanisms or combinations of the foregoing and need not be limited to the structure shown in the drawing. Stiffening rod lever 622 activates the forward and retractive movement of stiffening rod 608 from the first and second disc segment members and the combined discoid assembly. It will be understood that housed within handle 602 are the appropriate mechanisms, cams and gear assemblies necessary to engage, disengage and release the first and second disc segment members 102 and 101 within and/or from the intra spinal space.

Disc member insertion tool 600 and its component parts may be fabricated of various types of metals, metal alloys, plastics, ceramics and other suitable materials including combinations thereof typically used in the fabrication of surgical tools and the like. Preferably, tool 600 is relatively lightweight, durable, easily manipulated and is also inert (i.e. non-reactive to blood and other bodily fluids) and impervious. Preferably still, tool 600 may also be reusable in whole or in part and may therefore preferably be capable of sterilization by autoclave, gases, chemical disinfectants, radiation and other methods known for and useful for sterilizing surgical instruments.

Figure 14A:
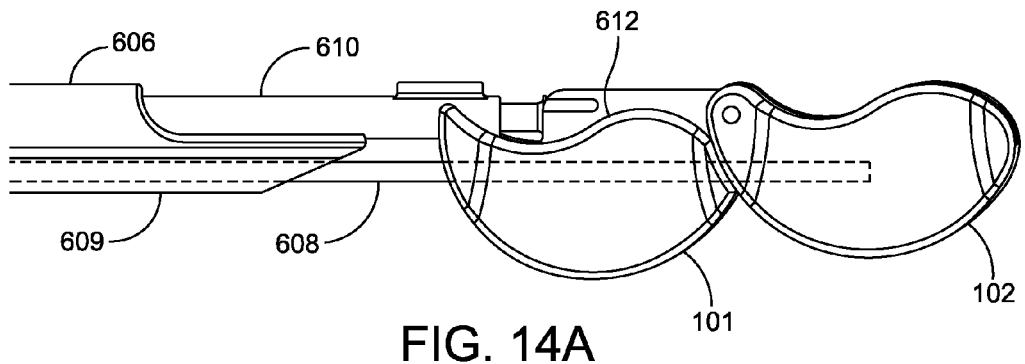
FIGS. 14 A-C show partial phantom view of first and second disc segments mounted on the distal end of the insertion tool shown in FIG. 13.
Figure 14B:
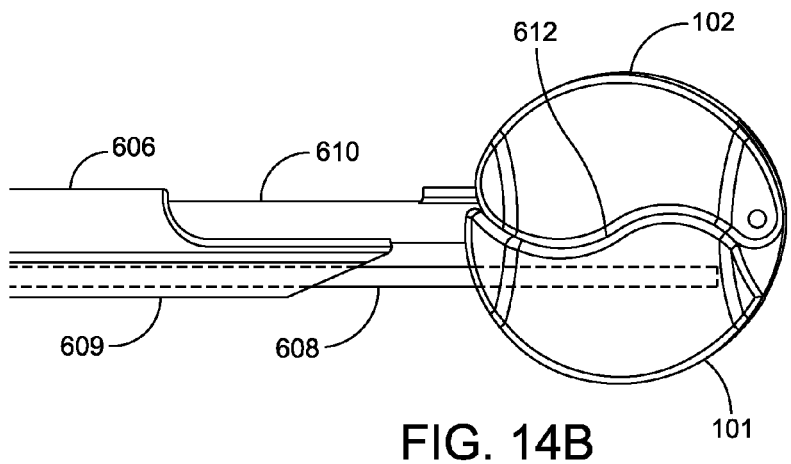
Figure 14C:
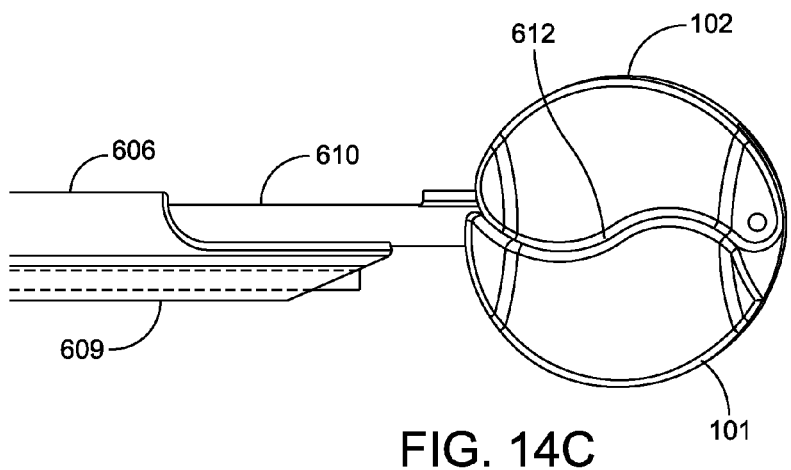

FIGS. 14 A-C show a series of close ups of the distal ends of insertion shaft housing 606, rod shaft housing 609, stiffening rod 608, insertion shaft 610 and tool head 612 of the disc member insertion tool 600 of FIG. 13 in operative connection with first and second disc segment members 102 and 101. Generally, insertion shaft 610 is rigid and fixed in length with stiffening rod 608 being capable of lateral directional movement independently of insertion shaft 610 during manipulation and insertion of the first and second disc segment member assembly. In this manner, both insertion shaft and stiffening rod act to stabilize and guide first and second disc segment members into the spinal space and effect rotational movement of the disc segment members forming the discoid assembly. It will be noted from FIGS. 14 A-C that when stiffening rod 608 is fully deployed the implant is capable of being moved into position into the spinal space. Referring specifically to stiffening rod 608, it is noted that in FIG. 14 A, stiffening rod 608 extends through both the second disc segment member and substantially into first disc segment member to provide sufficient rigidity to enable the first disc segment member to guide into a designated spinal space. In FIG. 14 B, stiffening rod is retracted into the half way position to prevent rotation when shaft tip 612 is engaged within the assembled discoid. In FIG. 14 C stiffening rod 608 is fully retracted and the insertion tool is ready to be removed.

Figure 15:
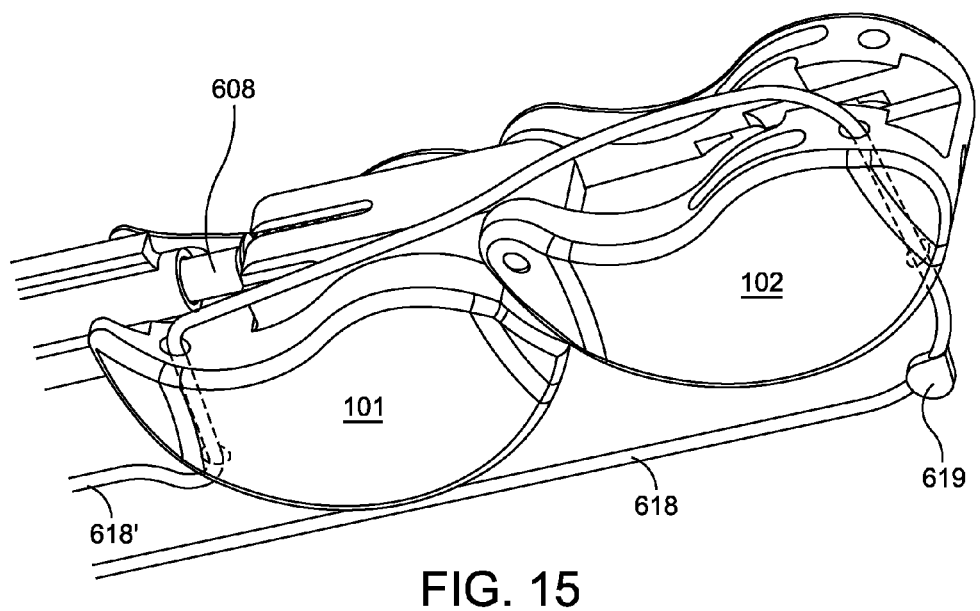
FIG. 15 depicts a close-up partial phantom perspective view of one embodiment of the first and second disc segments of the present disclosure showing a representative come-along closure mechanism.

FIG. 15 depicts a side perspective close-up and phantom view of first and second disc segment members positioned on the tool shown in FIG. 13. It will be appreciated that the drawings show substantially the same arrangement as that of FIG. 14 A with the addition of wire 618 and 618' shown threaded through the first and second disc segment members. It will be appreciated that one or more threading configurations and that a plurality of wires may be also employed in alternate embodiments. It will also be understood with reference to the figures that wire 618 and 618' follow a pathway and are operatively threaded within the wire conduits of the first and second disc segment members as generally set out in FIGS. 2-10.

Positioned at or near wire conduit 122 of first disc segment member 102 is bead 619. Bead 619 may also be a knot, ferrule, plug, clinch, buckle or any other constraint or shape incapable of passing through wire conduit 122. For reference purposes, it will be appreciated that wires 618 and 618' are continuous and the difference in designation refers to a direction of travel during the closure and assembly process. It will also be understood that the direction of travel of wire 618 will be towards the first disc segment member whereas the direction of travel of wire 618' will be in the opposite direction, namely, towards the associated tool. It will further be understood that the direction of movement of wire 618' proceeds rearwardly towards the tool, bead 619 will not be able to pass through wire conduit 122 and will cause rotation of the first disc segment member 102 about its pivot axis and enable closure of the first disc segment member 102 with second disc segment member 101. Once closure is complete, movement of wire 618' and 618 will occur in the opposite direction to enable removal of the wire from the discoid assembly.

Figure 16A:
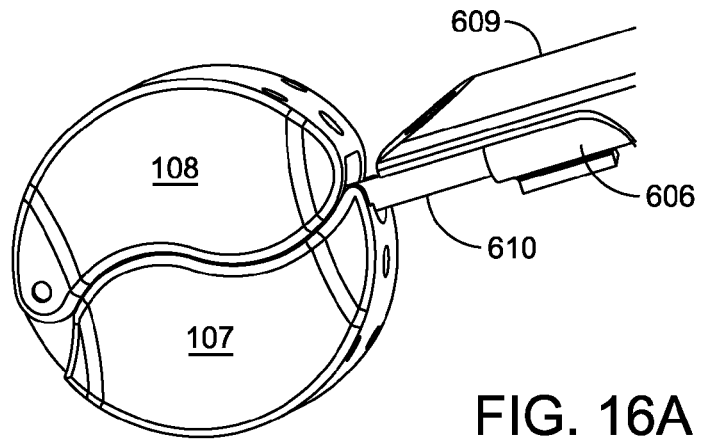
FIGS. 16 A-C are close up side views of the first and second disc segments during the de-coupling process for removal of the endoprosthesis.
Figure 16B:
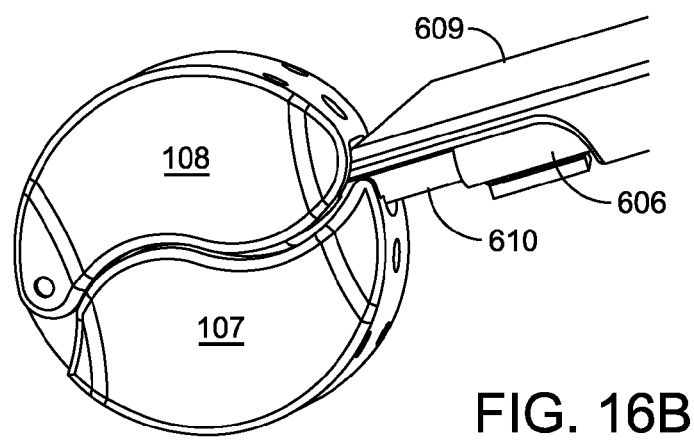
Figure 16C:
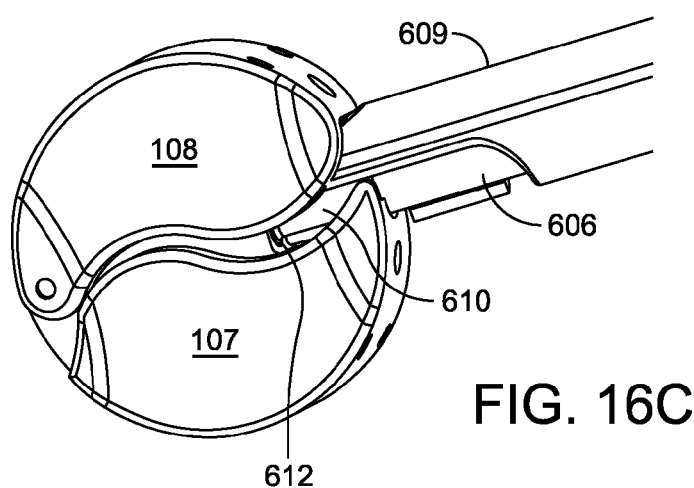

FIGS. 16 A-C show a series of close ups of the distal ends of insertion shaft housing 606, rod shaft housing 609, insertion shaft 610 and tool head 612 of the disc member insertion tool 600 of FIG. 13 in operative connection a discoid assembly during the disassembly process. In FIG. 16A insertion shaft 610 and tool head 612 are driven back into implant and secured by driving in a threaded anchor. As shown in FIG. 16 B, as the threaded anchor engages the discoid assembly, the beveled edge of rod shaft housing 609 is positioned to act as a wedge. As is shown more clearly in FIG. 16 C, the wedge is driven between implant halves and compressive fitments are subsequently unlocked.

Figure 17:
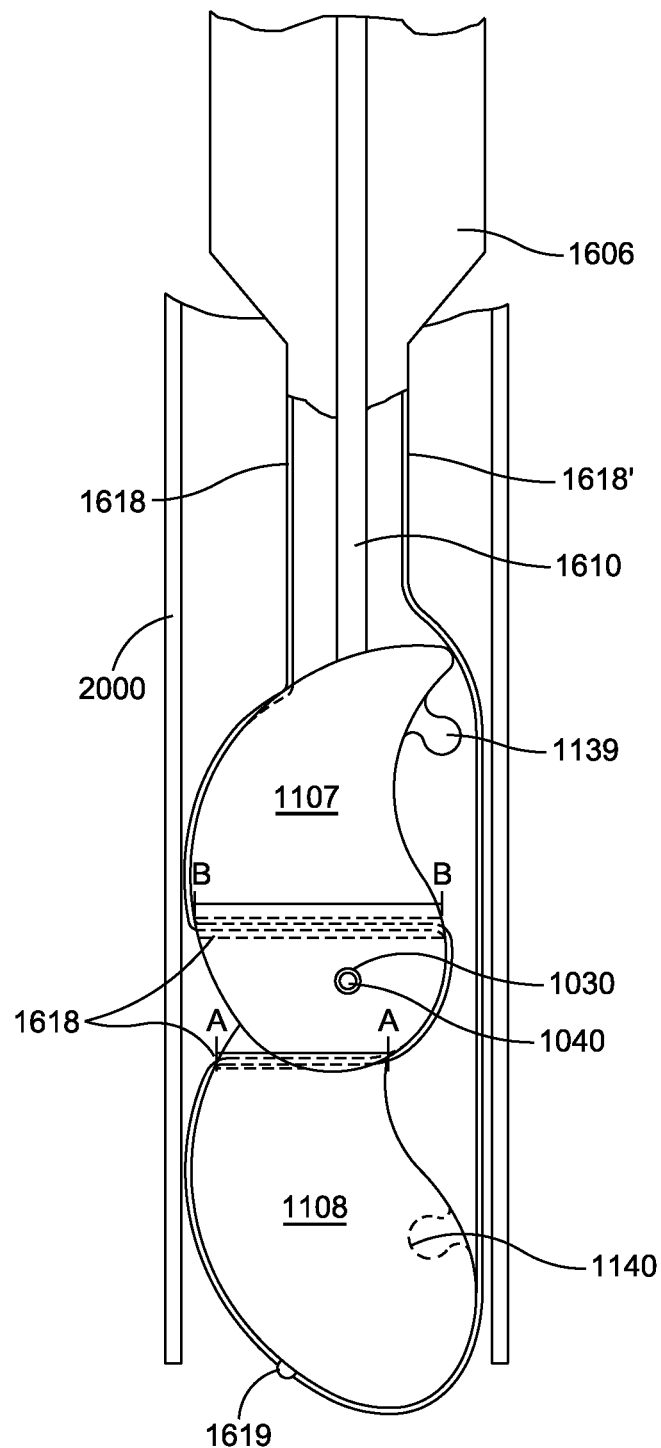
FIG. 17 is a side view of an alternate embodiment of the first and second disc segments of the present disclosure mounted on one embodiment of an insertion tool.

FIG. 17 is a partial phantom side view depicting one alternative embodiment of first disc segment member 1102 and second disc segment member 1101 positioned within delivery passageway 2000. As is shown in the drawing, the first and second disc segment members are hingedly connected via hinge member elements bore 1030 and pin 1040. It will be understood that the hinge member elements may also be formed internally on the interior surfaces of the first and second disc segment members whereas in other embodiments. Positioned in an insertion rod bore (not shown) at the trailing end of second disc segment member 1101 is insertion rod 1610 operatively connected on its opposite end to insertion tool 1606. Positioned on or near the trailing end interior wall surface of second disc segment member 1101 is projection 1139 which is formed to be mateably received by socket 1140 on the inner wall of the leading edge side of first disc segment member 1102. Projection 1139 and socket 1140 may generally be considered a "pop-bead" type of connection. Such pop bead connections define a generally semi rigid or ridged spherical ball formed on one end of a flexible neck extending from the inner surface wall of second disc segment member 1101. A complimentary socket is formed in the spherical body on the on the inner wall of the leading edge side of first disc segment member 1102 and defines a cavity and an opening into the cavity. The opening has a breadth slightly less than a breadth of the ball. The projection and socket are preferably formed of a flexible and resilient material so that the opening momentarily enlarges to admit the ball into the cavity when the ball is pressed there into operatively engaging in compressive fitment. The opening returns to its initial breadth to capture the ball in the cavity after the ball has passed through the opening. The opening also momentarily enlarges and returns to its initial breadth when the ball is removed therefrom by a pulling action.

Substantially parallel to insertion rod 1610 is wire 1618 and 1618' which follow the path defined by pathways A-A and B-B in first and second segment members, respectively. Wire 1618-1618' may also define bead 1619. As in other embodiments, bead 1619 may also be a knot, ferrule, plug, clinch, buckle or any other constraint or shape to operatively engage first disc member 1108. It will be understood after the first and second disc segment members are positioned within the spinal space, the direction of movement of wire 618' proceeds towards tool 1606, bead 1619 will cause rotation of the first disc segment member 1102 about its pivot axis and enable closure of the first disc segment member 1102 with second disc segment member 1101. Once closure is complete, movement of wire 1618' and 1618 will occur in the opposite direction to enable removal of the wire from the discoid assembly.

Figure 18:
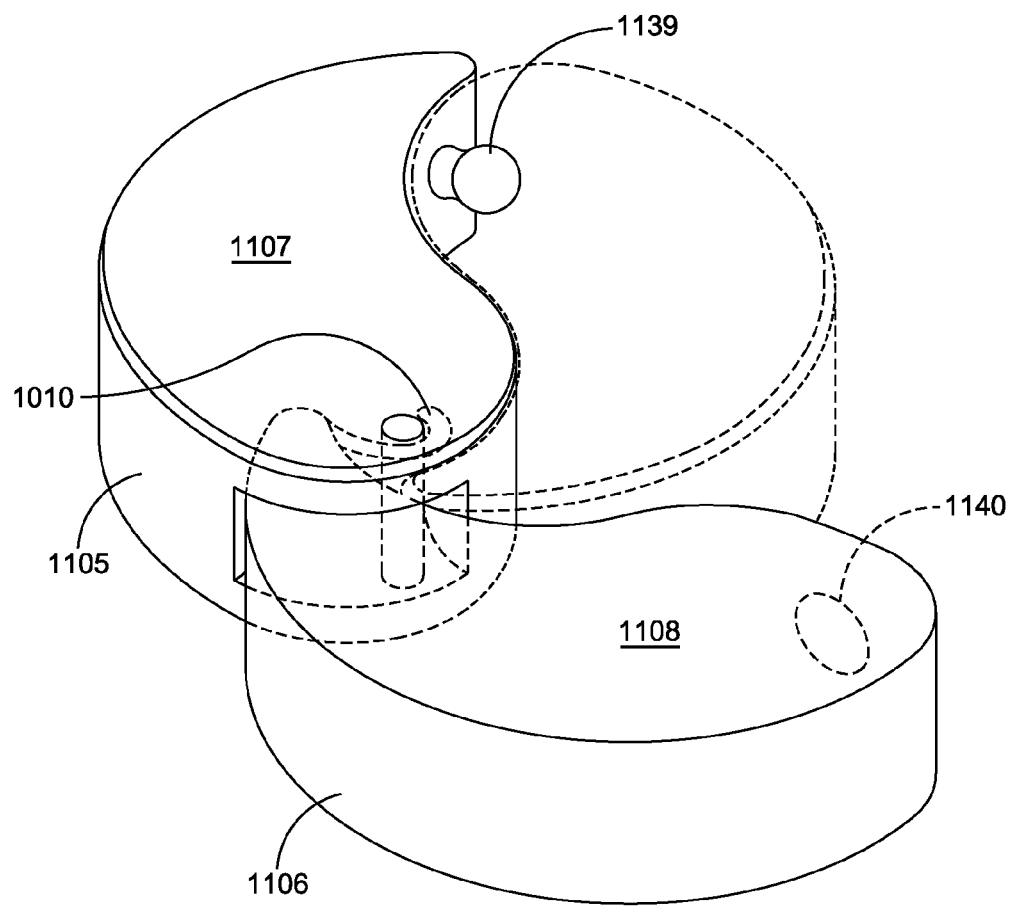
FIG. 18 is a dynamic partial phantom view of the first and second disc segments of the embodiment shown in FIG. 17.

FIG. 18 is a partial phantom axonometric projection perspective view of the embodiment shown in FIG. 17. The description and function of the various structures and landmarks recited above are incorporated by reference. It will however be appreciated from FIG. 18 how disc segment members 1101 and 1102 are cooperatively engaged to form a unified segment assembly which may be inserted into a spinal space as a single unit. It will likewise be appreciated that leading edge 1115 of second disc segment 1101 is configured to permit the pivoting rotation of the first disc member about the axis generally defined by hinge 1010.

From the foregoing detailed description and examples, it will be evident that modifications and variations can be made in the devices and methods of the disclosure without departing from the spirit or scope of the disclosure. Therefore, it is intended that all modifications and verifications not departing from the spirit of the disclosure come within the scope of the claims and their equivalents.

I claim:

1. An endoprosthesis for insertion into the annulus of a spinal disc comprising:
   a generally discoid assembly comprised of biocompatible materials having latitudinal and longitudinal axes, said discoid assembly formed by a plurality of complimentary hingedly connected tear-drop shaped bodies, each of said bodies having a curving pointed tip end and a blunt end opposite said pointed tip end mateably arranged along a common "s" shaped border in a congruent manner, said discoid assembly having upper and lower convex surfaces, said upper and lower convex surfaces having a curvature that generally corresponds with a pair of a human vertebral segments.

2. The endoprosthesis of claim 1 wherein said bodies are configured to join together and fit within the annulus upon implantation therein.

3. The endoprosthesis of claim 1 wherein said bodies further comprise a peripheral outer wall surface having a fixed radius of curvature and an inner wall surface having at least one concave portion and at least one convex portion adjacent thereto wherein said at least one concave portion is connected at one end to said outer wall and at least one adjacent convex portion is connected to the other end.

4. The endoprosthesis of claim 3 wherein said inner wall surface of said first tear drop shaped body further comprises a first mating face having at least one protrusion extending outwardly from the surface of said first body inner wall and wherein the second tear drop shaped body comprises a second mating face having at least one cavity extending inwardly on the surface of said second tear drop shaped body inner wall for receiving said protrusion from said first tear drop shaped body.

5. The endoprosthesis of claim 4 further comprising at least one cavity on of said the mating face of the first tear drop shaped body.

6. The endoprosthesis of claim 4 further comprising at least one protrusion on said the mating face of the second tear drop shaped body.

7. The endoprosthesis of claim 4 further comprising a fastener selected from the group of wire sutures, pop-bead connectors and screws.

8. The endoprosthesis of claim 7, wherein a radius of curvature of the outer peripheral face is substantially constant forming a substantially partially circular shape.

9. The endoprosthesis of claim 7, wherein a radius of curvature of the outer peripheral face is varying forming a substantially partially elliptical shape.

10. The endoprosthesis of claim 9, wherein the radius of curvature of the first and second convex and concave mating surfaces form a substantially partially elliptical shape.

11. The endoprosthesis of claim 7, wherein the first and second tear drop shaped body portions are joined together within the annulus upon implantation.

12. The endoprosthesis of claim 1 wherein said bodies further comprises at least one conduit for receiving a fastener.

13. The endoprosthesis of claim 12 wherein said fastener is selected from the group comprising suture wires, pop-bead connectors and threaded screws.

14. The endoprosthesis of claim 1 wherein said bodies further comprise at least one orifice for receiving an insertion tool.

15. An endoprosthesis for insertion into the annulus of a spinal disc comprising:
a pair of hingedly connected disc members comprising;
a first tear-drop shaped disc member having a first disc periphery including a fixed radius of curvature outer wall surface and an inner wall surface having at least one concave portion connected at one end to said outer wall surface and at least one adjacent convex portion connected to said opposite end of said outer wall surface of said first tear-drop shaped disc member, said first member inner wall surface having at least one mating member selected from the group of projections and cavities and a first hinge member;
a second tear-drop shaped disc member having a second disc periphery including a fixed radius of curvature outer wall surface and an inner wall surface having at least one concave portion connected at one end to said outer wall surface and at least one adjacent convex portion connected to said opposite end of said outer wall surface of said second tear-drop shaped disc member, said second member inner wall surface having at least one mating member selected from the group of projections and cavities and a second hinge member; and
wherein said first disc at least one mating member and said second disc at least one mating member each of said members having a curving pointed tip end and a blunt end opposite said pointed tip end and are mateably arranged along a common generally "s" shaped border in a congruent manner and secured to each other intradiscally with at least one fastener selected from the group of wire sutures, pop-bead connectors and screws, said discoid assembly further having upper and lower convex surfaces, said upper and lower convex surfaces having a curvature that generally corresponds with a pair of a human vertebral segments.

16. An endoprosthesis for insertion into an annulus of a spinal disc, said endoprosthesis comprising:
a body having a substantially discoid shape, the body including a first substantially tear-drop shaped body portion and a second substantially tear-drop shaped body portion pivotally connected thereto, each of said body portions having a curving pointed tip end and a blunt end opposite said pointed tip end, the first body portion having a first peripheral inner mating face having a first shape, the second body portion having a second peripheral inner mating face having a second shape that is complementary with the first peripheral inner mating face and wherein the first and second peripheral inner mating faces are aligned to each other intradiscally along a common generally "s" shaped border in a congruent manner.

17. The endoprosthesis of claim 16, wherein one of the first or second mating faces has a convex portion and the other of the first or second mating faces has a concave portion, the convex portion configured to matingly engage with the concave portion.

18. The endoprosthesis of claim 17, wherein the body has a curved outer peripheral face having a radius of curvature and wherein the first and second convex and concave mating faces having a radius of curvature which is less than the radius of curvature of the outer face.

19. The endoprosthesis of claim 17, wherein a radius of curvature of the first and second convex and concave mating surfaces form a substantially partially circular shape.

20. The endoprosthesis of claim 17, wherein the ratio of the radius of curvature of the first and second outer peripheral surfaces and the radius of curvature of the first and second inner convex and concave inner mating surfaces is less than or equal to 2:1.

21. The endoprosthesis of claim 16, wherein the first mating face of the first body portion has a first convex portion and a first concave portion and the second mating face has a second convex portion and a second concave portion, the first convex portion configured to matingly engage with second concave portion and the first concave portion configured to matingly engage with second convex portion.

22. The endoprosthesis of claim 16, wherein the body portions define at least one conduit configured to receive a tensioning wire configured to draw the body portions into mating engagement to form the discoid.

23. The endoprosthesis of claim 16, further comprising a lock configured to secure the body portions together in mating engagement to form the discoid.

24. The endoprosthesis of claim 23, wherein the lock defines [a] at least one protrusion formed on one of the first or second mating faces and [a] at least one complementary channel formed in the other of the first or second mating faces.

25. The endoprosthesis of claim 24, wherein the lock defines a first protrusion formed on and a first channel formed in the first mating face and a second protrusion formed on and a second channel formed in the second mating face, and wherein the first protrusion is configured to mate with the second channel and the second protrusion is configured to mate with the first channel.

26. The endoprosthesis of claim 24 wherein the at least one protrusion defines a substantially cylindrical boss and the at least one complementary channel defines a substantially cylindrical bore.

27. The endoprosthesis of claim 26, wherein an end of the protrusion and an edge which defines the channel are each chamfered.

28. The endoprosthesis of claim 26, wherein the at least one protrusion and a wall which defines at least one channel includes a lock ring.

29. The endoprosthesis of claim 26, wherein the at least one protrusion and a wall of at least one channel defines a conduit configured to receive a tensioning wire configured to draw the body portions into mating engagement to form the discoid.

30. The endoprosthesis of claim 24, wherein at least one protrusion and the wall of at least one channel define a conduit configured to receive a tensioning wire configured to draw the body portions into mating engagement to form the discoid.

31. An endoprosthesis for insertion into an annulus of a spinal disc, said endoprosthesis comprising:
a body having a substantially discoid shape, the body including:
a first substantially tear drop shaped body portion the first body portion having a curving pointed tip end and a blunt end opposite said pointed tip end and a first peripheral mating face having a first convex portion and a first concave portion;
a first hinge element on the body of the first body portion at or near said pointed tip end;
a second substantially tear drop shaped body portion having a second peripheral mating face having a curving pointed tip end and a blunt end opposite said pointed tip end and a second convex portion and a second concave portion, the first convex portion configured to matingly engage with second concave portion and the first concave portion configured to matingly engage with second convex portion;
a second hinge element on the body of the second body portion at or near said blunt end, said second hinge element operatively connected to said first hinge element; and
a lock configured to secure the first and second body portions together in mating engagement to form the discoid.

32. The endoprosthesis of claim 31, wherein the lock defines at least one protrusion formed on one of the first or second mating faces and a complementary channel formed in the other of the first or second mating faces.

33. The endoprosthesis of claim 31, wherein the lock defines a first protrusion formed on and a first channel formed in the first mating face and a second protrusion formed on and a second channel formed in the second mating face, and wherein the first protrusion is configured to mate with the second channel and the second protrusion is configured to mate with the first channel.

34. The endoprosthesis of claim 33, wherein the protrusion defines a boss and the complementary channel defines a bore.

35. The endoprosthesis of claim 34, wherein an end of the protrusion and an edge which defines the channel are each chamfered.

36. The endoprosthesis of claim 33, wherein one of the protrusions and a wall which defines the channel define a lock ring.

37. The endoprosthesis of claim 33, wherein the protrusion and a wall of the channel defines a conduit configured to receive a tensioning wire configured to draw the body portions into mating engagement to form the discoid.

38. The endoprosthesis of claim 33, wherein a plurality of protrusions and a plurality of walls of the channel define a conduit configured to receive a tensioning wire configured to draw the body portions into mating engagement to form the discoid.

39. An endoprosthesis for insertion into the annulus of a spinal disc, said endoprosthesis comprising:
a generally discoid assembly having latitudinal and longitudinal axes, said discoid assembly formed by a pair of substantially tear drop shaped complimentary bodies joined by an operative connection and mateably arranged along a generally "s" shaped common border in a congruent manner along the latitudinal axis, said discoid assembly having upper and lower convex surfaces, said upper and lower convex surfaces having a curvature that generally corresponds with a pair of a human vertebral segments.

40. The endoprosthesis of claim 39 wherein said operative connection is selected from the group comprising hinges, ball-and-socket assemblies, springs, swivels, flexible joints, universal joints, pivot assemblies and live articulations.

* * * * *